(12) United States Patent
Baek et al.

(10) Patent No.: US 11,166,675 B2
(45) Date of Patent: Nov. 9, 2021

(54) ELECTRONIC DEVICE AND METHOD FOR MEASURING VITAL SIGNAL

(71) Applicant: Samsung Electronics Co., Ltd., Gyeonggi-do (KR)

(72) Inventors: Hyun-Jae Baek, Seoul (KR); Jung-Taek Oh, Seoul (KR); Jae-Geol Cho, Gyeonggi-do (KR); Chul-Ho Cho, Gyeonggi-do (KR); Gun-Woo Jin, Gyeonggi-do (KR)

(73) Assignee: Samsung Electronics Co., Ltd

( * ) Notice: Subject to any disclaimer, the term of this patent is extended or adjusted under 35 U.S.C. 154(b) by 0 days.

(21) Appl. No.: 16/682,748

(22) Filed: Nov. 13, 2019

(65) Prior Publication Data

US 2020/0077952 A1    Mar. 12, 2020

Related U.S. Application Data

(62) Division of application No. 14/844,595, filed on Sep. 3, 2015.

(30) Foreign Application Priority Data

Sep. 3, 2014   (KR) .................. 10-2014-0117297
Jan. 6, 2015   (KR) .................. 10-2015-0001341
Jul. 17, 2015  (KR) .................. 10-2015-0101716

(51) Int. Cl.
*A61B 5/00*     (2006.01)
*A61B 5/0205*   (2006.01)

(52) U.S. Cl.
CPC .......... *A61B 5/681* (2013.01); *A61B 5/0205* (2013.01); *A61B 5/486* (2013.01); *A61B 5/4884* (2013.01);

(Continued)

(58) Field of Classification Search
CPC ..... A61B 5/0205; A61B 5/486; A61B 5/4884; A61B 5/681; A61B 5/721; A61B 5/7278; A61B 5/742
See application file for complete search history.

(56) References Cited

U.S. PATENT DOCUMENTS 5,001,461 A  *  3/1991  Vroom .................. A63C 11/005
                                                340/539.1
5,697,371 A     12/1997  Aoyagi
(Continued)

FOREIGN PATENT DOCUMENTS

CN    10167770     3/2010
CN    102065759    5/2011
(Continued)

OTHER PUBLICATIONS

Baek, Hyun Jae et al., Reliability of ultra short-term analysis as a surrogate of standard 5-minute analysis of heart rate variability.
(Continued)

*Primary Examiner* — Omer S Khan
(74) *Attorney, Agent, or Firm* — The Farrell Law Firm, P.C.

(57) ABSTRACT

Methods and apparatuses are provided for measuring a vital signal. An application is executed to output vital information of a user wearing an electronic device. Instructions are output that guide inhalation and exhalation of the user based on the executed application. At least one vital signal for the user is obtained while outputting the instructions. Vital information corresponding to the obtained at least one vital signal is output.

18 Claims, 34 Drawing Sheets

(52) U.S. Cl.
 CPC ............ *A61B 5/721* (2013.01); *A61B 5/7278* (2013.01); *A61B 5/742* (2013.01)

(56) References Cited

U.S. PATENT DOCUMENTS

| | | |
|---|---|---|
| 2007/0167850 A1 | 7/2007 | Russell et al. |
| 2008/0187163 A1* | 8/2008 | Goldstein ............ H04R 29/004 381/380 |
| 2008/0242415 A1* | 10/2008 | Ahmed ................... A63F 13/00 463/39 |
| 2008/0318624 A1 | 12/2008 | Hedtke et al. |
| 2010/0249864 A1 | 9/2010 | Jarverud et al. |
| 2010/0324427 A1 | 12/2010 | Devot et al. |
| 2012/0259182 A1 | 10/2012 | Kim et al. |
| 2013/0144111 A1* | 6/2013 | Wang ................. A61B 5/02416 600/27 |
| 2014/0088378 A1 | 3/2014 | Muzet |
| 2014/0094675 A1 | 4/2014 | Luna et al. |
| 2014/0206946 A1 | 7/2014 | Kim et al. |
| 2014/0249433 A1* | 9/2014 | Banet ....................... A61B 5/01 600/485 |
| 2015/0120205 A1* | 4/2015 | Jeon ....................... A61B 5/015 702/19 |
| 2016/0039424 A1* | 2/2016 | Hong .................... B60W 40/08 701/2 |
| 2016/0065831 A1* | 3/2016 | Howard ............. H04N 5/23203 348/211.2 |
| 2016/0346603 A1* | 12/2016 | Halliday .......... A63B 21/00189 |
| 2017/0011210 A1* | 1/2017 | Cheong ................ A61B 5/0022 |
| 2017/0319087 A1* | 11/2017 | Van De Laar ........ G06F 3/0482 |

FOREIGN PATENT DOCUMENTS

| | | |
|---|---|---|
| CN | 102490701 | 6/2012 |
| CN | 203252647 | 10/2013 |
| CN | 103717125 | 4/2014 |
| CN | 103961113 | 8/2014 |
| DE | 102012206293 | 10/2013 |
| JP | 2012-105762 | 6/2012 |
| KR | 100855473 | 9/2008 |
| KR | 1020100008875 | 1/2010 |
| KR | 100954817 | 4/2010 |
| KR | 1020120033777 | 4/2012 |
| KR | 1020120131898 | 12/2012 |
| KR | 1020130093925 | 8/2013 |
| TW | 201430731 | 8/2014 |
| WO | WO 2011/077097 | 6/2011 |
| WO | WO 2012/145430 | 10/2012 |
| WO | WO 2014/052987 | 4/2014 |

OTHER PUBLICATIONS

Telemedicine and e-Health, TMJ-2014-0104.R1, pp. 32.
International Search Report dated Dec. 9, 2015 issued in counterpart application No. PCT/KR2015/009198,11 pages.
European Search Report dated Jan. 12, 2016 issued in counerpart application No. 15183496.7-1657, 6 pages.
Taiwanese Office Action dated Jun. 17, 2019 issued in counterpart application No. 104128890, 19 pages.
Chinese Office Action dated Jun. 21, 2019 issued in counterpart application No. 201510558153.2, 29 pages.
Taiwanese Office Action dated Mar. 20, 2020 issued in counterpart application No. 104128890, 26 pages.

* cited by examiner

ELECTROCARDIOGRAM (ECG)

BALLISTOCARDIOGRAM (BCG)

Photoplethysmography (PPG)

Impedance Plethysmography

ELECTROCARDIOGRAM

BALLISTOCARDIOGRAM

| Table 3. Correlation Coefficient and Kruskal-Wallis Test for Time Domain Variables According to Different Durations of Input R-R Interval Series ||||||||||||
|---|---|---|---|---|---|---|---|---|---|---|---|
| VARIABLE, AGE GROUP | DATA LENGTH |||||||||||
| | 270 S | 240 S | 210 S | 180 S | 150 S | 120 S | 90 S | 60 S | 30 S | 20 S | 10 S |
| HR ||||||||||||
| 10 years | 0.9958[c] | 0.9943[c] | 0.9934[c] | 0.9907[c] | 0.9827[c] | 0.9695[c] | 0.9466[c] | 0.9421[c] | 0.8615[c] | 0.8084[c] | 0.7378[c] |
| 20 years | 0.9995[c] | 0.9983[c] | 0.9961[c] | 0.9941[c] | 0.9922[c] | 0.9897[c] | 0.9838[c] | 0.9767[c] | 0.9665[c] | 0.9625[c] | 0.9392[c] |
| 30 years | 0.9996[c] | 0.9988[c] | 0.9972[c] | 0.9944[c] | 0.9919[c] | 0.989[c] | 0.985[c] | 0.9814[c] | 0.9731[c] | 0.9663[c] | 0.9558[c] |
| 40 years | 0.9998[c] | 0.9991[c] | 0.998[c] | 0.9963[c] | 0.9938[c] | 0.9907[c] | 0.9877[c] | 0.9852[c] | 0.9732[c] | 0.9681[c] | 0.951[c] |
| 50 years | 0.9999[c] | 0.9996[c] | 0.9992[c] | 0.9985[c] | 0.9978[c] | 0.9956[c] | 0.9918[c] | 0.9859[c] | 0.9835[c] | 0.9814[c] | 0.9757[c] |
| 60 years | 1[c] | 0.9998[c] | 0.9995[c] | 0.9991[c] | 0.9984[c] | 0.9972[c] | 0.9964[c] | 0.9947[c] | 0.9851[c] | 0.9835[c] | 0.984[c] |
| Total | 0.9992[c] | 0.9984[c] | 0.9972[c] | 0.9955[c] | 0.993[c] | 0.9893[c] | 0.9835[c] | 0.9793[c] | 0.9622[c] | 0.952[c] | 0.9321[c] |
| SDNN ||||||||||||
| 10 years | 0.998[c] | 0.9917[c] | 0.9906[c] | 0.9808[c] | 0.9554[b] | 0.8616[b] | 0.8216[b] | 0.6736 | 0.7858 | 0.7295 | 0.728 |
| 20 years | 0.9938[c] | 0.9847[b] | 0.9536[b] | 0.9262[a] | 0.8859[a] | 0.8623 | 0.7867 | 0.7383 | 0.608 | 0.5657 | 0.5721 |
| 30 years | 0.9726[b] | 0.9511[a] | 0.9327 | 0.8706 | 0.8373 | 0.7981 | 0.7187 | 0.6198 | 0.5045 | 0.4393 | 0.2396 |
| 40 years | 0.9943[c] | 0.9816[c] | 0.9575[b] | 0.9419[b] | 0.9227[b] | 0.8971[a] | 0.8338 | 0.7344 | 0.6311 | 0.4936 | 0.1969 |
| 50 years | 0.9898[c] | 0.9738[c] | 0.9509[c] | 0.919[c] | 0.8802[c] | 0.6955[c] | 0.6307[c] | 0.5453[b] | 0.4626[b] | 0.4973[b] | 0.4596 |
| 60 years | 0.9991[c] | 0.9974[c] | 0.9969[c] | 0.9953[c] | 0.9887[c] | 0.9766[c] | 0.9356[c] | 0.8901[c] | 0.8781[b] | 0.8644[b] | 0.8681 |
| Total | 0.9949[b] | 0.9866[b] | 0.2396 | 0.9619 | 0.934 | 0.8531 | 0.802 | 0.7044 | 0.6971 | 0.664 | 0.6203 |
| RMSSD ||||||||||||
| 10 years | 0.9957[c] | 0.9928[c] | 0.9882[c] | 0.9666[c] | 0.9629[c] | 0.9184[c] | 0.9033[c] | 0.8255[b] | 0.8538[b] | 0.8014[b] | 0.7618 |
| 20 years | 0.9981[c] | 0.9862[c] | 0.9682[c] | 0.9508[c] | 0.9433[b] | 0.9281[b] | 0.8619[b] | 0.8348[b] | 0.7586[b] | 0.6379[b] | 0.6219[b] |
| 30 years | 0.9291[c] | 0.9043[c] | 0.8932[b] | 0.7884[b] | 0.7316[b] | 0.6754[b] | 0.6477[b] | 0.5588[b] | 0.3904[a] | 0.3261[a] | 0.2094[a] |
| 40 years | 0.998[c] | 0.994[c] | 0.9756[c] | 0.9416[c] | 0.9315[c] | 0.9143[c] | 0.8697[c] | 0.7531[b] | 0.7229[b] | 0.6238[a] | 0.4475 |
| 50 years | 0.9843[c] | 0.9783[c] | 0.9807[c] | 0.9648[c] | 0.9251[c] | 0.6876[c] | 0.6011[c] | 0.5767[c] | 0.5212[b] | 0.5189[b] | 0.4437[b] |
| 60 years | 0.9987[c] | 0.9946[c] | 0.9929[c] | 0.9901[c] | 0.9849[c] | 0.9793[c] | 0.9573[c] | 0.9431[c] | 0.8308[c] | 0.8116[c] | 0.7978[b] |
| Total | 0.9869[c] | 0.9797[c] | 0.9707[b] | 0.9427[b] | 0.929[b] | 0.8894[b] | 0.8608[b] | 0.8107[a] | 0.7716[a] | 0.7162 | 0.636 |
| pNN50 ||||||||||||
| 10 years | 0.9965[c] | 0.9895[c] | 0.9833[c] | 0.9685[c] | 0.9548[c] | 0.9237[c] | 0.8954[c] | 0.8586[c] | 0.793[c] | 0.7026[c] | 0.5226[c] |
| 20 years | 0.9977[c] | 0.9937[c] | 0.9888[c] | 0.9839[b] | 0.9753[b] | 0.9608[b] | 0.9477[b] | 0.9199[b] | 0.8641[b] | 0.8162 | 0.642 |
| 30 years | 0.9944[c] | 0.985[c] | 0.976[b] | 0.9624[b] | 0.947[b] | 0.929[b] | 0.9005 | 0.8451 | 0.7257 | 0.5361 | 0.4058 |
| 40 years | 0.9963[c] | 0.9933[c] | 0.9813[c] | 0.9759[c] | 0.9651[b] | 0.9464[b] | 0.9114[b] | 0.8538 | 0.7779 | 0.6809 | 0.5495 |
| 50 years | 0.9963[c] | 0.9891[c] | 0.9839[c] | 0.9708[c] | 0.9318[c] | 0.869[c] | 0.7991[c] | 0.6597[c] | 0.8562[b] | 0.8335[b] | 0.5139 |
| 60 years | 0.9995[c] | 0.998[c] | 0.9874[c] | 0.9868[c] | 0.972[c] | 0.9753[c] | 0.952[b] | 0.9634[b] | 0.9247[b] | 0.9247[b] | 0.9247[b] |
| Total | 0.9978[c] | 0.9938[c] | 0.9892[b] | 0.9831[b] | 0.9746[b] | 0.9604[b] | 0.9447[b] | 0.9168[b] | 0.8719 | 0.7994 | 0.6528 |

FIG.17A

| Table 4. Correlation Coefficient and Kruskal-Wallis Test for Frequency Domain Variables According to Different Durations of Input R-R Interval Series ||||||||||||
|---|---|---|---|---|---|---|---|---|---|---|---|
| VARIABLE, AGE GROUP | DATA LENGTH |||||||||||
| | 270 S | 240 S | 210 S | 180 S | 150 S | 120 S | 90 S | 60 S | 30 S | 20 S | 10 S |
| HR |||||||||||| 
| 10 years | 0.9987[c] | 0.9928[c] | 0.9893[c] | 0.9829[b] | 0.9636[c] | 0.9607[c] | 0.9014[b] | 0.4101 | 0.7083 | 0.6708[b] | 0.4430 |
| 20 years | 0.9964[c] | 0.9914[c] | 0.9519[c] | 0.9346 | 0.8706 | 0.8559[c] | 0.7732[c] | 0.7589 | 0.6934 | 0.5888 | 0.6081 |
| 30 years | 0.944[c] | 0.9311[b] | 0.9401[b] | 0.8637[a] | 0.8632[b] | 0.8547[a] | 0.7182[b] | 0.6425 | 0.5929 | 0.7051 | 0.4155 |
| 40 years | 0.9952[c] | 0.9846[c] | 0.9722[b] | 0.9618[b] | 0.9433[c] | 0.9166[c] | 0.8705[b] | 0.7902 | 0.6443 | 0.4854 | 0.0919 |
| 50 years | 0.992[c] | 0.9838[c] | 0.9632[c] | 0.9378[c] | 0.9477[c] | 0.8353[c] | 0.8127[c] | 0.7787[c] | 0.3215 | 0.2719[b] | 0.2284[a] |
| 60 years | 0.9996[c] | 0.9983[c] | 0.9987[c] | 0.9988[c] | 0.9987[c] | 0.9979[c] | 0.9862[c] | 0.942[c] | 0.9934[b] | 0.992[c] | 0.9921[c] |
| Total | 0.993[c] | 0.986[b] | 0.9703[b] | 0.9454 | 0.9195[c] | 0.929[b] | 0.8636[a] | 0.5338 | 0.6298 | 0.5813 | 0.4156 |
| SDNN ||||||||||||
| 10 years | 0.9916[c] | 0.993[c] | 0.9887[c] | 0.9566[c] | 0.9482[c] | 0.9295[c] | 0.8941[c] | 0.8886[b] | 0.8915[b] | 0.8445[b] | 0.8309 |
| 20 years | 0.9898[c] | 0.9793[c] | 0.9365[c] | 0.8979[b] | 0.9037[b] | 0.8852[c] | 0.8036[b] | 0.7495[c] | 0.6118[b] | 0.4249[b] | 0.4917[a] |
| 30 years | 0.9061[c] | 0.8836[c] | 0.8564[b] | 0.7467[c] | 0.6627[c] | 0.613[c] | 0.5902[c] | 0.5094[c] | 0.3876[c] | 0.3366 | 0.1465[b] |
| 40 years | 0.9948[c] | 0.9882[c] | 0.9773[c] | 0.9573[c] | 0.9243[c] | 0.8728[c] | 0.7987[c] | 0.6668[c] | 0.5913[b] | 0.426[b] | 0.2973 |
| 50 years | 0.9942[c] | 0.9898[c] | 0.9941[c] | 0.9858[c] | 0.8943[c] | 0.4613[c] | 0.2702[c] | 0.2263[c] | 0.1452[c] | 0.2028[c] | 0.1154[b] |
| 60 years | 0.9981[c] | 0.9946[c] | 0.9933[c] | 0.9904[c] | 0.9845[c] | 0.9811[c] | 0.9457[c] | 0.9407[c] | 0.5138[b] | 0.5079[c] | 0.5175[a] |
| Total | 0.9833[c] | 0.975[c] | 0.9538[b] | 0.9091[b] | 0.8635[b] | 0.8211[b] | 0.7784[b] | 0.7527[b] | 0.6919[a] | 0.6709[a] | 0.6294 |
| RMSSD ||||||||||||
| 10 years | 0.9998[c] | 0.9993[c] | 0.9991[c] | 0.9984[c] | 0.9925[b] | 0.8488[b] | 0.831[b] | 0.329 | 0.7061 | 0.7115 | 0.701 |
| 20 years | 0.9939[c] | 0.9844[b] | 0.9147[b] | 0.8788[b] | 0.8116[a] | 0.7778 | 0.6853 | 0.6771 | 0.4993 | 0.4284 | 0.5139 |
| 30 years | 0.9858[b] | 0.971[a] | 0.9541 | 0.9222 | 0.9099 | 0.8603 | 0.7296 | 0.5571 | 0.5156 | 0.4855 | 0.3614 |
| 40 years | 0.9957[c] | 0.9854[b] | 0.9596[b] | 0.9484[b] | 0.9431[b] | 0.9251[a] | 0.855 | 0.7662 | 0.6304 | 0.3781 | 0.0478 |
| 50 years | 0.9884[c] | 0.9587[c] | 0.9072[c] | 0.8391[c] | 0.7585[c] | 0.5376[b] | 0.4373[b] | 0.341[b] | 0.2184 | 0.2343 | 0.1792 |
| 60 years | 0.9996[c] | 0.9985[c] | 0.9982[c] | 0.9971[c] | 0.9933[c] | 0.9853[c] | 0.8831[c] | 0.7731[b] | 0.948[a] | 0.9456 | 0.9468 |
| Total | 0.9997[b] | 0.9989[a] | 0.9979 | 0.9968 | 0.9895 | 0.8216 | 0.7939 | 0.3495 | 0.5508 | 0.5574 | 0.5397 |
| pNN50 ||||||||||||
| 10 years | 0.9998[c] | 0.9994[c] | 0.9993[b] | 0.9992[b] | 0.9934[a] | 0.8296 | 0.672 | 0.1518 | 0.331 | 0.0369 | 0.0335 |
| 20 years | 0.9812[b] | 0.9517[b] | 0.7788[b] | 0.7276 | 0.6318 | 0.5984 | 0.4898 | 0.4718 | 0.1887 | 0.0914 | 0.0211 |
| 30 years | 0.9822[b] | 0.9661[a] | 0.9449 | 0.9254 | 0.9108 | 0.8696 | 0.6442 | 0.3724 | 0.3236 | 0.1157 | 0.088 |
| 40 years | 0.9917[c] | 0.9718[b] | 0.9371[b] | 0.9275[b] | 0.9141 | 0.8976 | 0.8245 | 0.7251 | 0.5742 | 0.2406 | 0.0584 |
| 50 years | 0.9938[c] | 0.9774[c] | 0.9508[b] | 0.9446[b] | 0.9297[b] | 0.9359[a] | 0.822[a] | 0.2806 | 0.2264 | 0.0513 | 0.5729 |
| 60 years | 0.9975[c] | 0.9989[c] | 0.9985[c] | 0.9896[c] | 0.9774[b] | 0.9454[b] | 0.6393[b] | 0.5274[b] | 0.8762 | 0.0886 | 0.0487 |
| Total | 0.9997[b] | 0.9991 | 0.9984 | 0.9979 | 0.9899 | 0.7943 | 0.6187 | 0.1688 | 0.2705 | 0.0319 | 0.0357 |

FIG.17B

| Table 4. Correlation Coefficient and Kruskal-Wallis Test for Frequency Domain Variables According to Different Durations of Input R-R Interval Series continued ||||||||||||
|---|---|---|---|---|---|---|---|---|---|---|---|
| VARIABLE, AGE GROUP | DATA LENGTH |||||||||||
| | 270 S | 240 S | 210 S | 180 S | 150 S | 120 S | 90 S | 60 S | 30 S | 20 S | 10 S |
| nLF ||||||||||||
| 10 years | 0.9756[c] | 0.9421[c] | 0.9197[c] | 0.87[b] | 0.8491[c] | 0.846[c] | 0.7549[c] | 0.6631[b] | 0.5197 | 0.4205[b] | 0.272[a] |
| 20 years | 0.9787[c] | 0.9632[c] | 0.9381[c] | 0.9081[c] | 0.9048[c] | 0.8631[c] | 0.8622[c] | 0.7861 | 0.6694 | 0.5812 | 0.4137 |
| 30 years | 0.9245[c] | 0.9009[c] | 0.8895[c] | 0.8585[b] | 0.8378[c] | 0.782[b] | 0.7663[c] | 0.6924 | 0.5841 | 0.4226 | 0.3478 |
| 40 years | 0.9885[c] | 0.9735[c] | 0.9758[c] | 0.9487[b] | 0.9356[c] | 0.91[c] | 0.8695[c] | 0.7442[a] | 0.6694 | 0.382 | 0.3331 |
| 50 years | 0.9921[c] | 0.9635[c] | 0.9553[c] | 0.8976[c] | 0.8947[c] | 0.8562[c] | 0.8344[c] | 0.88059[c] | 0.5987[a] | 0.6211[b] | 0.2704[c] |
| 60 years | 0.9861[c] | 0.9807[c] | 0.9774[c] | 0.9766[c] | 0.9816[c] | 0.9492[c] | 0.9099[c] | 0.8874[c] | 0.7945[c] | 0.7798[c] | 0.7334[b] |
| Total | 0.9725[c] | 0.9555[c] | 0.945[c] | 0.9167[b] | 0.9048[b] | 0.8696[b] | 0.8452[b] | 0.7652 | 0.6676 | 0.5065 | 0.3869 |
| nHF ||||||||||||
| 10 years | 0.9756[c] | 0.9421[c] | 0.9197[c] | 0.87[b] | 0.8491[c] | 0.846[c] | 0.7549[c] | 0.6631[b] | 0.5197 | 0.4205[b] | 0.272[a] |
| 20 years | 0.9787[c] | 0.9632[c] | 0.9381[c] | 0.9081[c] | 0.9048[c] | 0.8631[c] | 0.8622[c] | 0.7861 | 0.6694 | 0.5812 | 0.4137 |
| 30 years | 0.9245[c] | 0.9009[c] | 0.8895[c] | 0.8585[b] | 0.8378[c] | 0.782[b] | 0.7663[c] | 0.6924 | 0.5841 | 0.4226 | 0.3478 |
| 40 years | 0.9885[c] | 0.9735[c] | 0.9758[c] | 0.9487[b] | 0.9356[c] | 0.91[c] | 0.8695[c] | 0.7442[a] | 0.6694 | 0.382 | 0.3331 |
| 50 years | 0.9921[c] | 0.9635[c] | 0.9553[c] | 0.8976[c] | 0.8947[c] | 0.8562[c] | 0.8344[c] | 0.88059[c] | 0.5987[a] | 0.6211[b] | 0.2704[c] |
| 60 years | 0.9861[c] | 0.9807[c] | 0.9774[c] | 0.9766[c] | 0.9816[c] | 0.9492[c] | 0.9099[c] | 0.8874[c] | 0.7945[c] | 0.7798[c] | 0.7334[b] |
| Total | 0.9725[c] | 0.9555[c] | 0.945[c] | 0.9167[b] | 0.9048[b] | 0.8696[b] | 0.8452[b] | 0.7652 | 0.6676 | 0.5065 | 0.3869 |
| LF/HF ||||||||||||
| 10 years | 0.9787[c] | 0.8524[c] | 0.8359[c] | 0.7633[b] | 0.7293[c] | 0.786[c] | 0.6887[c] | 0.5086[b] | 0.2746 | 0.3359[b] | 0.0776[a] |
| 20 years | 0.9797[c] | 0.9762[c] | 0.949[c] | 0.9496[c] | 0.9068[c] | 0.8934[c] | 0.7541[c] | 0.6992 | 0.4299 | 0.4555 | 0.2398 |
| 30 years | 0.9818[c] | 0.9816[c] | 0.9443[c] | 0.9312[b] | 0.9179[c] | 0.8991[b] | 0.8475[c] | 0.796 | 0.546 | 0.5237 | 0.1518 |
| 40 years | 0.9579[c] | 0.9535[c] | 0.9468[c] | 0.9347[b] | 0.8958[c] | 0.9194[c] | 0.8339[c] | 0.7579[a] | 0.493 | 0.2275 | 0.1259 |
| 50 years | 0.9807[c] | 0.9687[c] | 0.9334[c] | 0.8109[c] | 0.7878[c] | 0.7331[c] | 0.6831[c] | 0.6441[c] | 0.5845[a] | 0.5579[b] | 0.1032[c] |
| 60 years | 0.9854[c] | 0.9294[c] | 0.8677[c] | 0.8585[c] | 0.8451[c] | 0.8403[c] | 0.7982[c] | 0.7723[c] | 0.6901[c] | 0.7668[c] | 0.7914[b] |
| Total | 0.9782[c] | 0.9761[c] | 0.9466[c] | 0.9317[b] | 0.9101[b] | 0.8933[b] | 0.8151[b] | 0.7153 | 0.5308 | 0.3717 | 0.1503 |

FIG.17C

ELECTRONIC DEVICE AND METHOD FOR MEASURING VITAL SIGNAL

PRIORITY

This application is a Divisional Application of U.S. patent application Ser. No. 14/844,595, filed in the U.S. Patent and Trademark Office on Sep. 3, 2015, which claims priority under 35 U.S.C. § 119(a) to Korean Application Serial Nos. 10-2014-0117297, 10-2015-0001341 and 10-2015-0101716, which were filed in the Korean Intellectual Property Office on Sep. 3, 2014, Jan. 6, 2015, and Jul. 17, 2015, respectfully, the contents of each of which are incorporated herein by reference.

BACKGROUND

1. Field of the Invention

The present invention relates generally to an electronic device and a method for signal measurement, and more particularly, to an electronic device and method for determining vital information from a measured a vital signal.

2. Description of the Related Art

In order to increase the value of an electronic device and meet various demands of users, various applications have been developed for execution by the electronic device.

A user can measure his/her own vital signals relating to health care through an electronic device. Methods for measuring a vital signal include, for example, electrocardiogram (ECG), photoplethysmography (PPG), ballistocardiogram (BCG), and impedance plethysmography. Since a heart rate measurement method is noninvasive and includes various pieces of health-related information, it is considered as an optimal measurement method for mobile health care. Through the heart rate measurement method, heart rate variability (HRV) may be measured. A balance level of the autonomic nervous system of the sympathetic nervous system and the parasympathetic nervous system may be monitored through the HRV.

When the HRV is measured, a calculation of a stress index generally only determines an increase/decrease of the corresponding parameter.

For example, in one measurement method, stress may be determined through a parameter in a frequency domain of the HRV. In order to analyze the HRV in the frequency domain, a minimum measurement time of two (2) minutes is required, and it is not easy to apply such a required time period to a mobile heath care device.

In another measurement method, in addition to the stress index, a fatigue index and a heath index may be calculated using the HRV. Indexes may be replaced with blood sugar level, blood pressure, body temperature, and weight, but it is impossible to analyze the HRV by using the blood sugar level, blood pressure, body temperature, and weight.

In an additional measurement method, it may require five (5) minutes to analyze a frequency area of the HRV, and non-linearity and an analysis is performed by reading an ECG from a memory. However, when a stress index is measured, different personal HRVs are not reflected and the same method is applied, so that individual variance is not reflected to the stress measurement.

The above-described methods are only applicable to an on-demand product that a user operates with an intention to measure stress. Further, in order to measure stress, the user should remain still, without any movement, for a minimum of two (2) minutes or longer. However, except for a case where the user intentionally measures stress, no movement for two (2) minutes or longer is unlikely.

SUMMARY

The present invention has been made to address at least the above problems and/or disadvantages and to provide at least the advantages described below. Accordingly, an aspect of the present invention provides an electronic device and a method for measuring a vital signal.

In accordance with an aspect of the present invention, a method is provided for measuring a vital signal by an electronic device. An application is executed to output vital information of a user wearing the electronic device. Instructions are output that guide inhalation and exhalation of the user based on the executed application. At least one vital signal for the user is obtained while outputting the instructions. Vital information corresponding to the obtained at least one vital signal is output.

In accordance with another aspect of the present invention, an electronic device is provided for measuring a vital signal. The electronic device includes a sensor unit configured to obtain at least one vital signal. The electronic device also includes at least one processor configured to execute an application to output vital information of a user wearing the electronic device, output instructions that guide inhalation and exhalation of the user based on the executed application, obtain, via the sensor unit, at least one vital signal for the user while outputting the instructions, and output vital information corresponding to the obtained at least one vital signal.

In accordance with another aspect of the present invention, a non-transitory computer readable medium is provided with computer executable instructions stored thereon executed by at least one processor to perform the method of measuring a vital signal by an electronic device. The method includes executing an application to output vital information of a user wearing the electronic device, outputting instructions that guide inhalation and exhalation of the user based on the executed application, obtaining at least one vital signal for the user while outputting the instructions, and outputting vital information corresponding to the obtained at least one vital signal.

BRIEF DESCRIPTION OF THE DRAWINGS

The above and other aspects, features, and advantages of the present invention will be more apparent from the following detailed description when taken in conjunction with the accompanying drawings, in which:

FIG. 17A is a diagram illustrating a correlation for each age range between a result of an analysis of parameters in a time domain based on standard 5-minute length data and a result of an analysis of the parameters based on data of different lengths, according to an embodiment of the present invention;

FIGS. 17B and 17C are diagrams illustrating a correlation for each age range between a result of an analysis of parameters in the frequency domain based on standard 5-minute length data and a result of an analysis of the parameters based on data of different lengths, according to an embodiment of the present invention;

DETAILED DESCRIPTION

Figure 1:
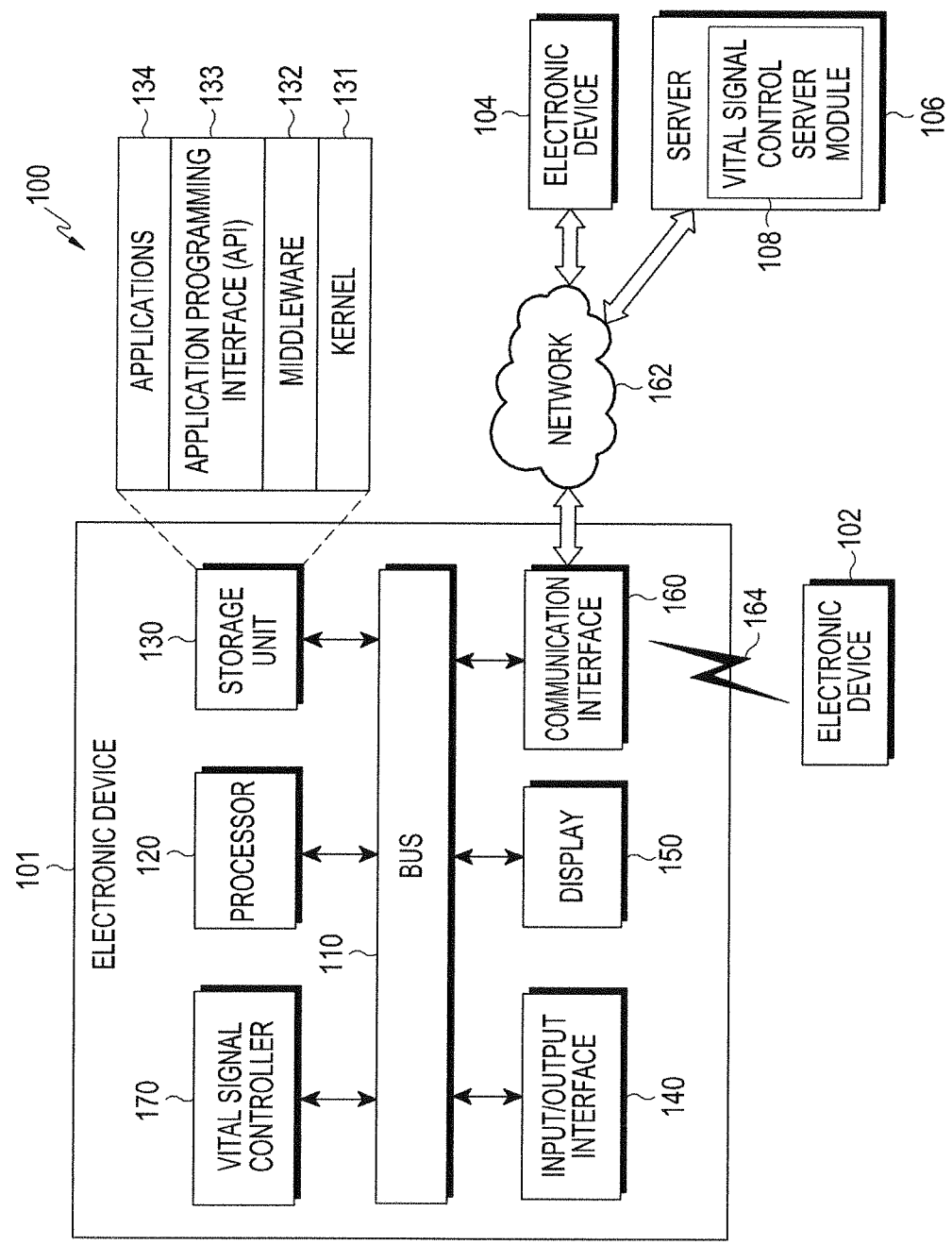
FIG. 1 is a diagram illustrating a network environment including an electronic device, according to an embodiment of the present invention.

Embodiments of the present invention are described in detail with reference to the accompanying drawings. The same or similar components maybe designated by the same or similar reference numerals although they are illustrated in different drawings. Detailed descriptions of constructions or processes known in the art may be omitted to avoid obscuring the subject matter of the present invention.

Herein, the expressions "include", "have", "may include", and "may have" refer to the existence of a corresponding function, operation, or element, and do not exclude the existence of one or more additional functions, operations, or elements.

Herein, the expression "or" includes any or all combinations of words enumerated together. For example, the expression "A or B" may include A, may include B, or may include both A and B.

Herein, expressions including ordinal numbers, such as "first" and "second," may modify various elements. However, such elements are not limited by the above expressions. For example, the above expressions do not limit the sequence and/or importance of the elements. The above expressions are used merely for the purpose of distinguishing an element from the other elements. For example, a first user device and a second user device indicate different user devices, although both are user devices. For example, a first element may be referred to as a second element, and similarly, a second element may be referred to as a first element, without departing from the scope of the present invention.

When an element is referred to as being "connected to" or "accessed by" other elements, it should be understood that the element may be directly connected to or accessed by the other elements, or another element may exist between them. Contrarily, when an element is referred to as being "directly coupled" or "directly connected" to any other element, it should be understood that no element is interposed therebetween.

As used herein, singular forms are intended to include the plural forms as well, unless the context clearly indicates otherwise.

Unless defined otherwise, all terms used herein, including technical and scientific terms, have the same meanings as those commonly understood by those of skill in the art to which the present disclosure pertains. Such terms as those defined in a generally used dictionary are to be interpreted to have the same meanings as the contextual meanings in the relevant field of art, and are not to be interpreted to have ideal or excessively formal meanings unless clearly defined in the present disclosure.

An electronic device, according to an embodiment the present invention, may be a device including a display control function. For example, the electronic device may be embodied as at least one of a smart phone, a tablet personal computer (PC), a mobile phone, a video phone, an e-book reader, a desktop PC, a laptop PC, a netbook computer, a personal digital assistant (PDA), a portable multimedia player (PMP), an MP3 player, a mobile medical device, a camera, a wearable device (for example, a head-mounted-device (HMD) such as electronic glasses, electronic clothes, an electronic bracelet, an electronic necklace, an electronic appcessory, an electronic tattoo, and a smart watch).

According to an embodiment of the present invention, the electronic device may be embodied as a smart home appliance with a display control function. The smart home appliance may include at least one of, for example, a television, a digital versatile disc (DVD) player, an audio player, a refrigerator, an air conditioner, a vacuum cleaner, an oven, a microwave oven, a washing machine, an air cleaner, a set-top box, a TV box, a game console, an electronic dictionary, an electronic key, a camcorder, and an electronic picture frame.

According to an embodiment of the present invention, the electronic device may include at least one of various medical devices such as, for example, a magnetic resonance angiography (MRA) scanner, a magnetic resonance imaging (MRI) scanner, a computed tomography (CT) scanner, a scanner, an ultrasonograph, or the like, a navigation device, a global positioning system (GPS) receiver, an event data recorder (EDR), a flight data recorder (FDR), a vehicle infotainment device, an electronic equipment for ship (for example a ship navigation device and gyro-compass and the like, avionics, a security device, a head unit for vehicle, an industrial or household robot, an automatic teller machine (ATM) in a banking facilitys or a point of sales (POS) device in a store.

According to an embodiment of the present invention, the electronic device may be embodied as at least one of furniture or a part of a building/structure, an electronic board, an electronic signature receiving device, a projector, and various types of measuring devices (for example, a water meter, an electricity meter, a gas meter, a radio wave meter and the like) including a display control function. The electronic device. according to an embodiment of the present invention, may be a combination of one or more of the aforementioned devices. Also, the electronic device may be a flexible device. Further, it is obvious to those skilled in the art that the electronic device is not limited to the aforementioned devices.

Hereinafter, an electronic device, according to various embodiments of the present invention, will be described with reference to the accompanying drawings. The term "user", as used herein, may refer to a person who uses an electronic device or a device (for example, an artificial intelligence electronic device) that uses an electronic device.

FIG. 1 is a diagram illustrating a network environment including an electronic device, according to an embodiment of the present invention.

Referring to FIG. 1, an electronic device 101 includes a bus 110, a processor 120, a storage unit 130, an input/output interface 140, a display 150, a communication interface 160, and a vital signal controller 170.

An electronic device, according to an embodiment of the present invention, may include various electronic devices capable of transmitting and receiving data, and executing a predetermined operation by transmitting or receiving a vital signal. Further, the electronic device may include a wearable device worn on a particular part of the human body to measure a vital signal, to store a measurement result therein, or to transmit the measured vital signal to smart phone, a mobile phone, or a notebook.

The bus 110 may be a circuit to connect the above-described components and to transfer communication (for example, control messages) between the above-described components.

The processor 120 may receive commands from other components (for example, the storage unit 130, the input/output interface 140, the display 150, the communication interface 160, or the vital signal controller 170) through the bus 110, analyze the received commands, and execute calculation or data processing according to the analyzed commands.

The storage unit 130 may store commands or data received from or generated by the processor 120 or other components (for example, the input/output interface 140, the display 150, the communication interface 160, or the vital signal controller 170). The storage unit 130 includes programming modules, for example, a kernel 131, middleware 132, an application programming interface (API) 133, applications 134, or the like. Each of the aforementioned programming modules may be formed of software, firmware, hardware, or a combination of at least two thereof.

The kernel 131 may control or manage system resources (for example, the bus 110, the processor 120, the storage unit 130, or the like) used to execute operations or functions implemented by the remaining other programming modules, for example, the middleware 132, the API 133, or the applications 134. Furthermore, the kernel 131 may provide an interface through which the middleware 132, the API 133, and the applications 134 may access individual components of the electronic device 101 to control or manage them.

The middleware 132 may act as a relay to allow the API 133 or the applications 134 to communicate with the kernel 131 to exchange data. Further, in association with task requests received from the applications 134, the middleware 132 may control (for example, scheduling or load-balancing) the task requests by using, for example, a method of assigning at least one of the applications 134 a priority for using system resources (for example, the bus 110, the processor 120, the storage unit 130, or the like) of the electronic device 101.

The API 133 is an interface through which the applications 134 control functions provided from the kernel 131 or the middleware 132, and may include, for example, at least one interface or function (for example, an instruction) for file control, window control, image processing, text control, or the like.

According to an embodiment of the present disclosure, the applications 134 may include a short message service (SMS)/multimedia messaging service (MMS) application, an email application, a calendar application, an alarm application, a health care application (for example, application measuring a quantity of exercise or blood sugar), an environmental information application (for example, application providing information associated with pressure, humidity, temperature, or the like), or the like. Additionally or alternatively, the applications 134 may be an application related to an information exchange between the electronic device 101 and an external electronic device (for example, a first external electronic device 102 and/or a second external electronic device 104). The electronic device 101 and the first external electronic device 102 may be connected through wired/wireless communication 164, and the electronic device 101 and the second external electronic device 104 may be connected through a network 162. The application related to information exchange may include, for example, a notification relay application for transferring predetermined information to the external electronic device or a device management application for managing the external electronic device.

For example, the notification relay application may include a function of transmitting notification information generated by another application (for example, SMS/MMS application, email application, health care application, or environment information application) of the electronic device 101 to the external electronic device 102 and/or 104. Additionally or alternatively, the notification relay application may receive notification information from, for example, an external electronic device (for example, the electronic device 104) and provide the same to a user. The device management application may manage (for example, install, remove, or update) at least a part of functions (for example, turning on/off the external electronic device (or some components of the external electronic device) or controlling a brightness of the display) of the external electronic device 104 communicating with the electronic device 101, an application executed in the external electronic device, or a service (for example, call service or message service) provided by the external electronic device.

According to an embodiment of the present invention, the applications 134 may include applications, which are designated according to attributes (for example, the type of electronic device) of the external electronic device 102 and/or 104. For example, when the external electronic device is an MP3 player, the application 134 may include an application related to the reproduction of music. Similarly, when the external electronic device is a mobile medical device, the applications 134 may include an application related to health care. According to an embodiment of the present invention, the applications 134 may include at least one of an application designated to the electronic device 101 and an application received from an external electronic device 102, 104, or a server 106.

The input/output interface 140 may transmit commands or data input from the user through an input/output device (for example, a sensor, a display, a keyboard, or touch screen) to the processor 120, the storage unit 130, the communication interface 160, or the vital signal controller 170 through, for example, the bus 110. For example, the input/output interface 140 may provide the processor 120 with data relating to a user's touch, which is input through the touch screen. The input/output interface 140 may output, through the input/output device (for example, a speaker or a display), commands or data received, from the processor 120, the memory 130, the communication interface 160, or the vital signal controller 170 through, for example, the bus 110. For example, the input/output interface 140 may output voice data processed by the processor 120 to the user through the speaker.

The display 150 may display various pieces of information (for example, multimedia data, text data, or the like) to the user.

The communication interface 160 may provide communication between the electronic device 101 and an external device 102, 104, or the server 106. For example, the communication interface 160 may be connected to the network 162 through wireless or wired communication to communicate with an external device (e.g., the second external electronic device 104 or the server 106). The wireless communication may include at least one of, for example, Wi-Fi, Bluetooth (BT), near field communication (NFC), GPS, and cellular communication (for example, long term evolution (LTE), LTE-advanced (LTE-A), code division multiple access (CDMA), wideband CDMA (WCDMA), universal mobile telecommunication system (UMTS), wireless broadband (WiBro), and global system for mobile communication (GSM)). The wired communication may include at least one of, for example, a universal serial bus (USB), a high definition multimedia interface (HDMI), recommended standard 232 (RS-232), and a plain old telephone service (POTS).

According to an embodiment of the present invention, the network 162 may be a telecommunication network. The telecommunication network may include at least one of a computer network, the Internet, the Internet of Things (IoT), and a telephone network. According to an embodiment of the present invention, a protocol (for example, transport layer protocol, data link layer protocol, or physical layer protocol) for the communication between the electronic device 101 and the external device 102 or 104 may be supported by at least one of the applications 134, the API 133, the middleware 132, the kernel 131, and the communication interface 160.

Each of the first and second external electronic devices 102 and 104 may be a device which is the same as or different from the electronic device 101. According to an embodiment of the present invention, the server 106 may include a group of one or more servers. According to an embodiment of the present invention, all or some of the operations performed by the electronic device 101 may be performed by another electronic device or a plurality of electronic devices 102, 104, or the server 106. According to an embodiment of the present invention, when the electronic device 101 should perform some functions or services automatically or by request, the electronic device 101 may make a request, to another device 102, 104, or the server 106, for performing at least some of the functions related to the functions or services, in addition to or instead of performing the functions or services by itself. The other electronic device 102, 104, or the server 106 may carry out the requested function or the additional function, and transfer the result to the electronic device 101. The electronic device 101 may provide the requested functions or services based on the received result as it is or after processing the received result. To this end, for example, cloud computing, distributed computing, or client-server computing technology may be used.

The server 106 includes a vital signal control server module 108 capable of supporting the vital signal controller 170 implemented in the electronic device 101. For example, the vital signal control server module 108 may include at least one component of the vital signal controller 170 to perform (for example, perform as a proxy) at least one of the operations performed by the vital signal controller 170.

The vital signal controller 170 may process at least a part of the information obtained from other component elements (for example, processor 120, storage unit 130, input/output interface 140, or communication interface 160), and provide the processed information to the user in various ways. For example, the vital signal controller 170 may control at least some functions of the electronic device 101 using the processor 120, or independently from the processor 120, so that the electronic device 101 may interwork with other electronic devices 104 or the server 106. According to an embodiment of the present invention, at least one component of the vital signal controller 170 may be included in the server 106 (for example, the vital signal control server module 108), and at least one operation implemented in the vital signal controller 170 may be supported by the server 106. The vital signal module 170 is described in greater detail below with reference to FIGS. 2 to 19.

Figure 2:
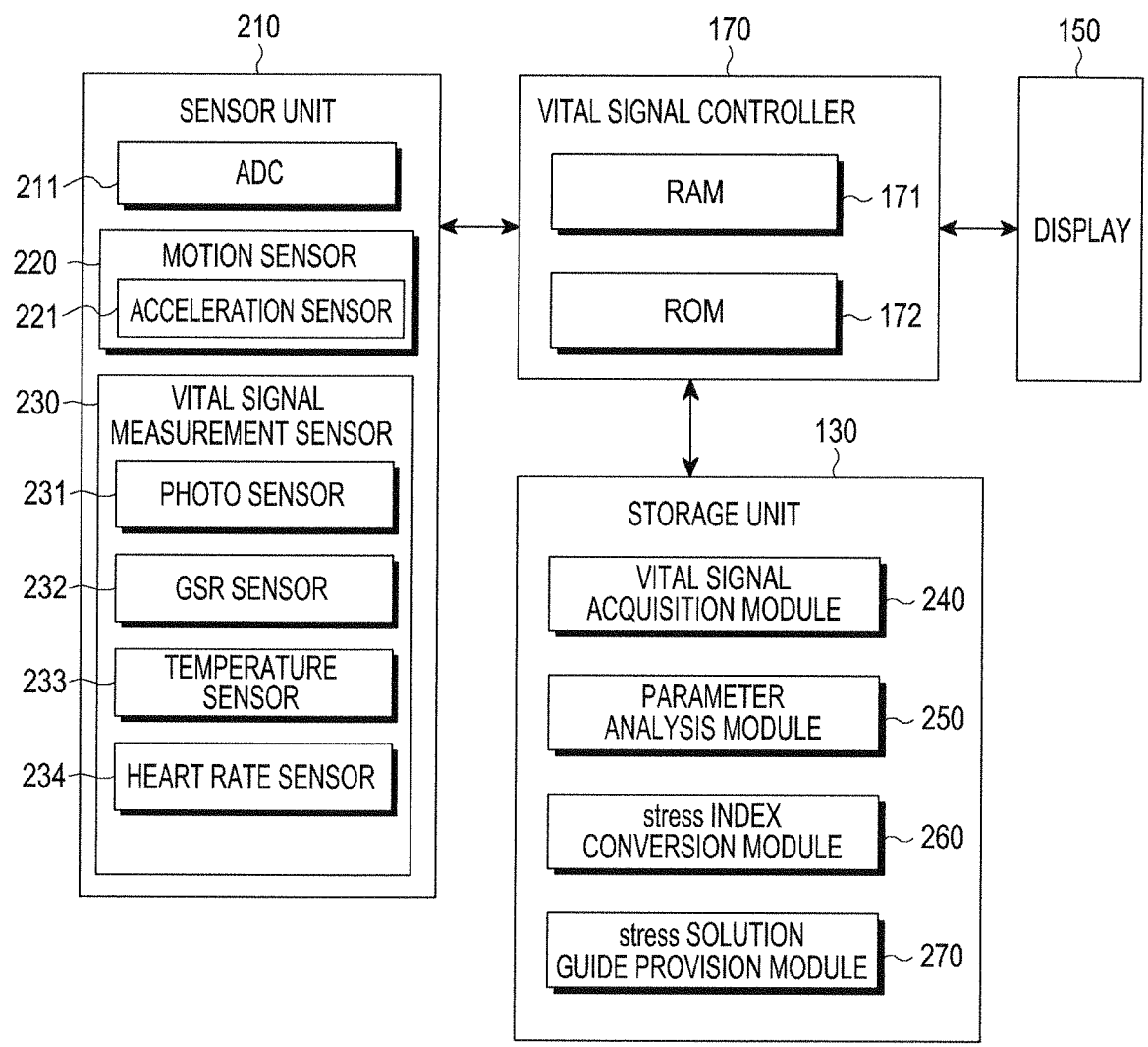
FIG. 2 is a block diagram illustrating an electronic device that measures a vital signal, according to an embodiment of the present invention.

FIG. 2 is a block diagram illustrating an electronic device that measures a vital signal, according to an embodiment of the present invention.

Referring to FIG. 2, the electronic device 101 measuring the vital signal, according to an embodiment of the present invention, includes a sensor unit 210, the storage unit 130, the display 150, and the vital signal controller 170.

The sensor unit 210 includes a motion sensor 220, a vital signal measurement sensor 230, and an analog to digital converter (ADC) 211. The sensor unit 210 may read a sensing value by turning on each sensor when needed. Further, the ADC 211 may be included in the sensor unit or separately included in the electronic device 101. The motion sensor 220 includes a sensor for detecting a motion, such as, for example, an acceleration sensor 221 or a gyro sensor. The motion sensor 220, according to an embodiment of the present invention, may further include various sensors for detecting a motion as well as the acceleration sensor 221 and the gyro sensor. Further, the vital signal measurement sensor 230 includes, for example, a photo sensor 231, a galvanic skin response (GSR) sensor 232, a temperature sensor 233, and a heart rate sensor 234. The vital signal measurement sensor 230, according to an embodiment of the present invention, may also include additional various sensors for measuring a user's vital signal.

The motion sensor 220 may output a data value according a motion of the electronic device 101. According to an embodiment of the present invention, the acceleration sensor 221 may include a biaxial (x and y axes) acceleration sensor or a triaxial (x, y, and z axes) acceleration sensor.

The vital signal measurement sensor 230 may measure various vital signals of the human body and output various sensor values related to the human body. According to an embodiment of the present invention, the vital signal measurement signal 230 may measure various vital signals to determine whether the electronic device 101 is worn on the human body and output a vital sensor value corresponding to the measured signal.

The photo sensor 231 may convert a light or information included in the light into an electrical signal. The photo sensor 231 may include a light emitting unit and a light receiving unit, and may emit a light through the light emitting unit and receive a light through the light receiving unit. The photo sensor 231 may be in close proximity to or may contact part of the human body when the electronic device 101 is worn on the human body. When the electronic device 101 is in close proximity to or contacts the part of the human body, the photo sensor 231 may irradiate the light emitted through the light emitting unit to the human body and receive a light generated by reflecting the light irradiated to the human body or by allowing the light irradiated to the human body to pass through the human body by the light receiving unit. The photo sensor 231 may output the light through the light emitting unit and then measure and output a light amount of the light received through the light receiving unit. The measured light amount may be used for determining whether the photo sensor 231 is in close proximity to or contacts the part of the human body, and whether the photo sensor 231 is in close proximity to or contacts the part of the human body may be used for determining whether the electronic device 101 is worn on the human body. Alternatively, the photo sensor 231 may be used for measuring the vital signal through an increase/decrease in the amount of the light received through the light receiving unit. For example, the photo sensor 231 may be used for measuring a blood pressure or a heart rate through PPG.

The GSR sensor 232 may include a GSR response sensor. The GSR sensor 232 may be one of an electrodermal response (EDR) sensor, a psycho galvanic reflect (PGR) sensor, a skin conductance response (SCR) sensor. The GSR sensor 232 may include an ohmmeter and may measure electrical conductivity between two points of the skin. When the electronic device 101 is worn on the human body, the photo sensor 232 may be in close proximity to or contact part of the human body. When the GSR sensor 232 is in close proximity to or contacts the part of the human body, the GSR sensor 232 may allow a predetermined small current to flow in the skin of the human body and then measure electrical conductivity between two points of the skin and output a skin resistance value. The measured electrical conductivity may be used for determining whether the GSR sensor 232 is in close proximity to or contacts the part of the human body, and whether the GSR sensor 232 is in close proximity to or contacts the part of the human body may be used for determining whether the electronic device 101 is worn on the human body.

The temperature sensor 233 may be a sensor that, when an internal resistance value, voltage value, or current value is changed by a temperature change, measures a temperature by using the changed internal resistance value, voltage value, or current value. When the electronic device 101 is worn on the human body, the temperature sensor 233 may be in close proximity to or contact part of the human body. When the temperature sensor 233 is in close proximity to or contacts the part of the human body, the temperature sensor 233 may output the changed internal resistance value, voltage value, or current value by the heat of the human body. The measured changed internal resistance value, voltage value, or current value may be used for determining whether the temperature sensor 233 is in close proximity to or contacts the part of the human body, and whether the temperature sensor 233 is in close proximity to or contacts the part of the human body may be used for determining whether the electronic device 101 is worn on the human body.

The heart rate sensor 234 may measure the vital signal associated with the heart rate through a mechanical, an electrical, or an optical method. The heart rate sensor 234 may include an ECG sensor for measuring ECG, a BCG sensor for measuring BCG, or a phonocardiography sensor for converting a vibration generated by the heart or big blood vessels into an electrical signal. Further, the heart rate sensor 234, according to an embodiment of the present invention, may further include various sensors for measuring a user's vital signal as well as the aforementioned sensors. The vital signal measurement sensor 230 may include an HRV sensor for measuring a pulse wave signal.

The storage unit 130 includes a vital signal acquisition module 240, a parameter analysis module 250, a stress index conversion module 260, and a stress solution guide provision module 270. At least one of the vital signal acquisition module 240, the parameter analysis module 250, the stress index conversion module 260, and the stress solution guide provision module 270 may be loaded to the vital signal controller 170 in accordance with the operation of at least one sensor included in the sensor unit 210.

The vital signal controller 170 may include a read only memory (ROM) 172 that stores a control program for controlling the electronic device 101, and a random access memory (RAM) 171 that is used as a storage area for storing a signal or data input from the outside of the electronic device 101, or for work performed in the electronic device 101. The vital signal controller 170 may include a single core, a dual core, a triple core, or a quadruple core. A central processing unit (CPU), the ROM 172, and the RAM 171 may be connected to each other through an internal bus.

When at least one sensor included in the sensor unit 210 operates, the vital signal controller 170 may load the corresponding module into the RAM 171 and perform at least one function performed by each module. A function performed by at least one of the vital signal acquisition module 240, the parameter analysis module 250, the stress index conversion module 260, and the stress solution guide provision module 270 may be performed by the processor 120, and the vital signal controller 170 may be referred to as a controller.

According to an embodiment of the present invention, the vital signal controller 170 may acquire a vital signal measured by the sensor unit 210, analyze a parameter of the acquired vital signal, convert the analyzed parameter into vital information, compare a converted stress index with a stress index at the same age range as that of the user of the measured vital signal, and output a result of the comparison.

The vital signal controller 170 may acquire the vital signal from the sensor unit 210 at least one time. The vital signal controller 170 may detect a motion of the electronic device 101 to acquire the vital signal and, when the motion is smaller than a predetermined (or preset) threshold, acquire the vital signal from the sensor unit 210. The predetermined threshold may be variably controlled. The vital signal controller 170 may receive information on whether breathing detected through at least one sensor included in a sensor module, and information on a breathing rate to determine that breathing is detected and analyze the breathing rate.

When the motion is smaller than the threshold, the vital signal controller 170 may measure the vital signal for a predetermined time (for example, 30 seconds) to analyze a parameter of the vital signal. When the motion smaller than the threshold lasts, the vital signal controller 170 may continuously measure the vital signal for the predetermined time. When the motion smaller than the threshold lasts for a time (for example, 10 seconds) shorter than the predetermined time to calculate a vial signal parameter, the vital signal controller 170 may measure the vital signal only for a section of time during which no motion is generated. The vital signal controller 170 may add values of each of a plurality of vital signals of time sections in which the vital signals are measured, an interval between the time sections being shorter than a predetermined time, and analyze parameters of the added values of the vital signals. When two sections, which are not continuous with each other, are separated by an interval shorter than a predetermined threshold, the vital signal controller 170 may continuously combine the sections and use the combined sections to calculate the parameter of the vital signal. For example, when non-continuous sections in which the vital signal is measured correspond to 10 seconds, 15 seconds, and 5 seconds, and data sections are separated by an interval shorter than or equal to a predetermined time (for example, 1 minute), the vital signal controller 170 may combine the sections to generate 30 seconds and use it to calculate the vital signal parameter. Further, the predetermined threshold may be variably controlled.

The vital signal controller 170 may acquire the vital signal at least once and analyze the acquired parameter of the vital signal. The vital signal controller 170 may analyze the parameter in the time domain of the acquired vital signal and analyze a variation of the parameter by using an interval between beats of the vital signal. The vital signal may include at least one of a heartbeat, a pulse, an impedance plethysmography, a BCG, an ECG, a PPG, and a blood flow rate. The parameter may include at least one of a heart rate (HR), an RR interval, a standard deviation of N-N intervals (SDNN), a root mean of sum of squared differences (RMSSD), and a percent of successive normal NN intervals difference greater than 50 msec (pNN50). The heartbeat interval may include at least one of an RR interval, a pulse interval, and a JJ interval of the vital signal. The RR interval refers to an interval between two peaks of the ECG, the JJ interval refers to an interval between two peaks of the BCG, and the pulse interval refers to an interval between two peaks of the impedance plethysmography and the PPG.

The vital signal controller 170 may convert the analyzed parameter into vital information (for example, a stress index) by taking the natural logarithm (ln) of a reciprocal of the parameter. The vital signal controller 170 may convert the analyzed parameter into the vital information by taking the natural logarithm of a value generated by dividing 1000 by the HRV. The vital signal controller 170 may compare the converted stress index with a stress index at the same age range as that of the user of which the vital signal is measured. The vital signal controller 170 may receive a user's age, and compare the converted stress index with an average stress index at the same age or the same age range as that of the user of which the converted stress index is input. Through the comparison, it may be determined whether the stress index of the user of which the vital signal is measured is higher or lower than the average stress index at the same age or the same age range. The average stress index may be pre-stored in the electronic device 101 or received from the server 106.

The vital signal controller 170 may compare the converted stress index with the average stress index at the same age or the same age range as that of the input user and output a result of the comparison through the display 150. The vital signal controller 170 may output the result of the comparison through at least one of a sound, vibration, and graphic user interface (GUI). The vital signal controller 170 may generate a guide indicating a breathing method to reduce the stress based on the result of the comparison and output the generated guide through the display 150. When the converted stress index is higher than the stress index at the same age range, the vital signal controller 170 may generate and output a guide to reduce the stress index. When the converted stress index is lower than the stress index at the same age range, the vital signal controller 170 may generate and output a guide indicating that the stress index is lower and including information useful for health. The guide may include at least one of information to reduce the stress index, an alarm informing that the stress index is higher, and a breathing method to reduce the stress index. When breathing is detected from the user in a state where the guide is output, the vital signal controller 170 may compare the detected breathing with the guide in real time and output a result thereof. The vital signal controller 170 may score the stress index that is changed by the detected breathing and output the stress index that is changed according to breathing, so as to allow the user to recognize the change in the stress index by the breathing.

Further, the vital signal controller 170 may store the converted stress index. The vital signal controller 170 may calculate an average of the stress indexes based on at least one of time zones, dates, days of the week, months, and years, and store the average in the storage unit 130. The storage unit 130 may store the converted stress index in real time according to the vital signal measured by the user, and calculate and store the average of the stored stress indexes based on at least one of time zones, dates, days of the week, months, and years. Further, the storage unit 130 may store the average stress index for each age range (for example, teens, twenties, thirties . . . ), periodically or aperiodically receive the average stress index from the server 106, and store the received average stress index.

According to an embodiment of the present invention, the vital signal acquisition module 240 may acquire at least one vital signal measured by the sensor unit 210, as described above. The vital signal acquisition module 240 may measure the vital signal in real time and transfer the measured value to the parameter analysis module 250.

According to an embodiment of the present invention, the parameter analysis module 250 may analyze the parameter of the vital signal through the vital signal received from the vital signal acquisition module 240, as described above. The parameter analysis module 250 may transfer a result of the analysis to the stress index conversion module 260.

According to an embodiment of the present invention, the stress index conversion module 260 may convert the parameter received from the parameter analysis module 250 to vital information, as described above.

According to an embodiment of the present invention, the stress solution guide provision module 270 may generate a guide including a result of the comparison between the stress index of the user received from the stress index conversion module 260 and the stress index at the same age range as that of the user.

At least one function performed by each of the vital signal acquisition module 240, the parameter analysis module 250, the stress index conversion module 260, and the stress solution guide provision module 270 may be performed by the vital signal controller 170 or the processor 120.

Figure 3A:
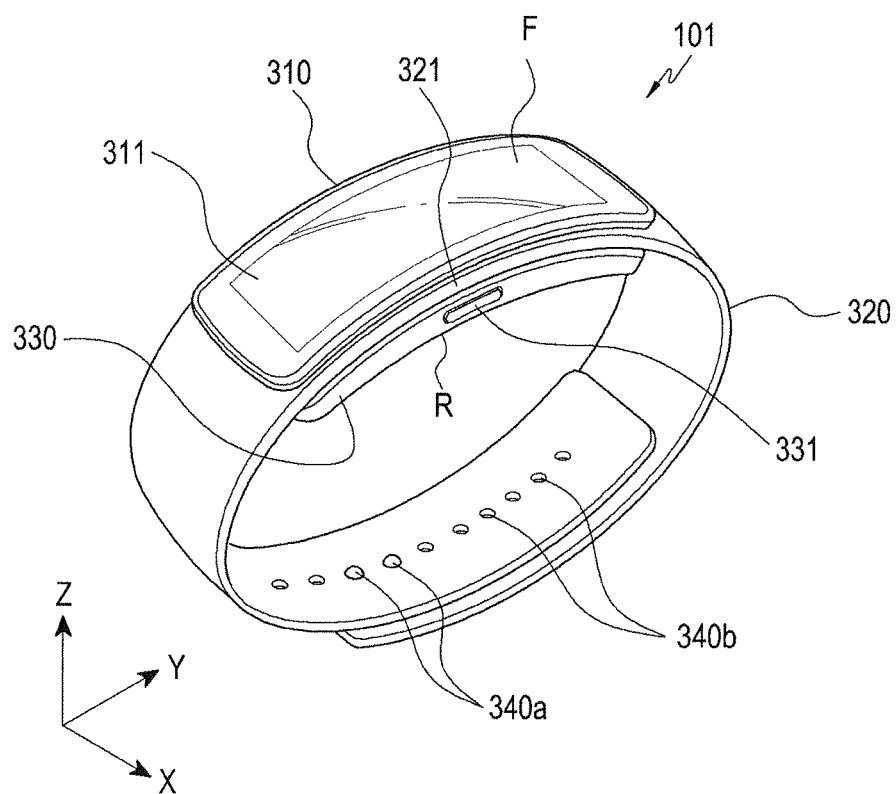
FIG. 3A is a diagram illustrating a perspective view of the electronic device, according to an embodiment of the present invention.
Figure 3B:
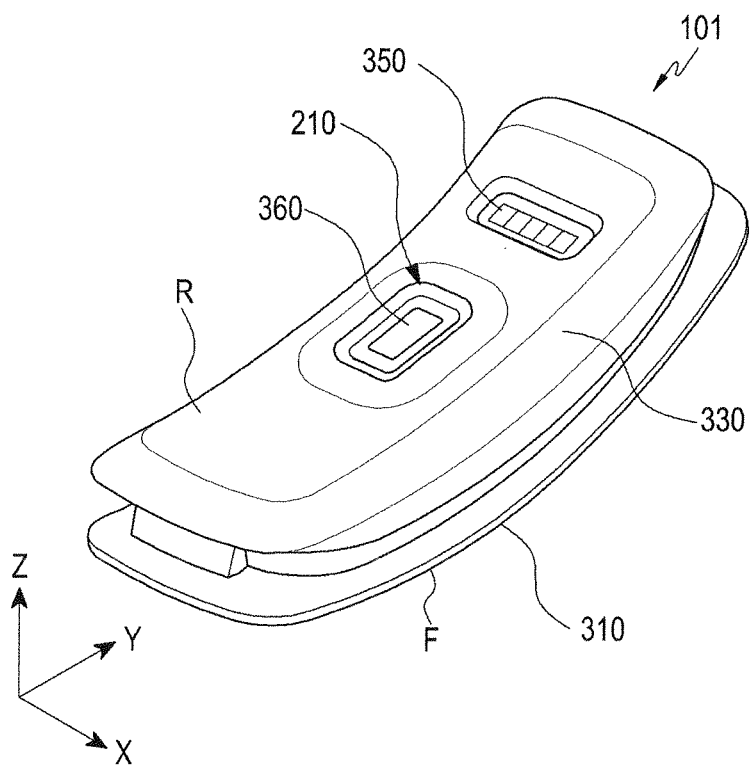
FIG. 3B is a diagram illustrating a perspective view of a part of the electronic device, according to an embodiment of the present invention.
Figure 3C:
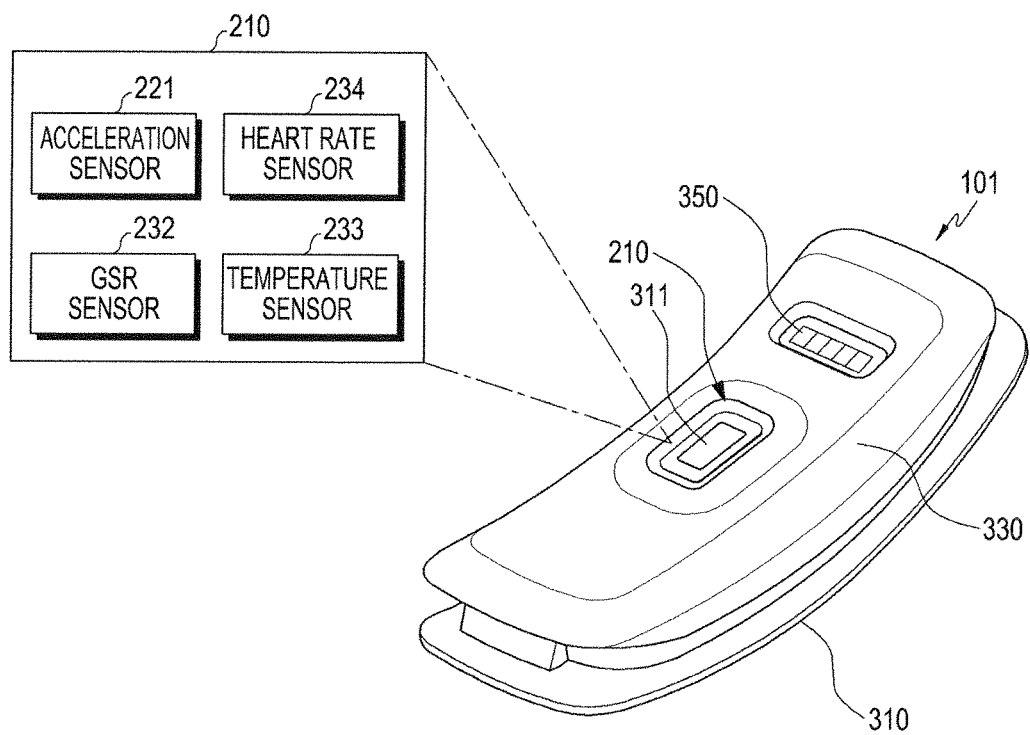
FIG. 3C is a diagram illustrating a sensor module of the electronic device, according to an embodiment of the present invention.

FIG. 3A is a diagram illustrating a perspective view of the electronic device, according to an embodiment of the present invention. FIG. 3B is a diagram illustrating a perspective view of a part of the electronic device, according to an embodiment of the present invention. FIG. 3C is a diagram illustrating a sensor module of the electronic device, according to an embodiment of the present invention.

Referring to FIG. 3A, the electronic device 101 may be worn as, for example, a watch, an arm band, a hair band, or an anklet. However, embodiments of the present disclosure are not limited thereto, and the electronic device 101 may also be embodied as a bracelet, a strip, a band, a mounted type (band-aid type) band, a belt, ear mounted earphones, a headphone, a cloth type, a shoe type, an HMD, a hat type, a glove type, a thimble type (finger-tip mounted type), a clip type, an arm band type, a contact lens device, digital clothes, and a remote control. Further, the electronic device 101 may be applied to a part of the user's body having curvature. For example, a part of the user's body having the curvature may include a wrist or an ankle. Further, the electronic device worn on various parts of the user's body according to a configuration of the wearing part.

The electronic device 101, according to an embodiment of the present invention, includes a body part 310 and a wearing part 320 including wearing members, such as a band or a strap. The body part 310 may be configured to be coupled to or separated from the wearing part 320. A display device 311 for displaying various pieces of information, a press key (for example, a side key 331), a sensor unit (for example, the vital signal measurement sensor), and/or a touch input unit may be disposed on the body part 310. The body part 310 includes a front surface F and a rear surface R, which contacts the user's body when worn on the user's body. The display device 311 is disposed on the front surface F of the body part 310, and the sensor unit is disposed on at least one of the rear surface R of the body part 310 and the wearing part 320.

The body part 310 may be a bar type and may have a curvature that at least partially corresponds to the user's body. For example, the body part 310 may have a rectangular shape substantially extending in a vertical direction (Y axis direction) and a curvature. Coupling grooves that engage with the wearing part 320 may be formed on a side surface of the body part 310. The coupling grooves may include a plurality of grooves formed on the side surface of the body part 310 or may have a closed curve shape extending along a circumference of the body part 310.

The wearing part 320 may be formed with an elastic material, and may allow the body part 310 to be stably worn on the user's body while in close contact with the skin of the user's body. Further, the body part 310 may be configured to be removable from the wearing part 320, and thus the wearing part 320 may be replaced. According to an embodiment of the present invention, a seat part 321 of the wearing part 320, which is coupled to the body part 310, may be configured to be elastically deformed, and an internal surface of the wearing part 320, which closely contacts the user's body, may not be formed with the elastic material. The wearing part 320 includes an opening that extends in one direction and from which the body part 310 is removable. The seat part 321 is configured to surround the circumference of the opening. When the body part 310 is coupled to the wearing part 320, at least a part of the seat part 321 is inserted into the coupling grooves extending along the side surface of the body part 310.

First and second wearing members 340a and 340b are separated from at least a part of the seat part 321 in the vertical direction (Y) of the body part 310. However, when the electronic device 101 is worn on the user's body, the first and second wearing members 340a and 340b have a curved form in a thickness direction (Z) of the body part 310 with respect to the seat part 321. Further, the wearing part 320 includes a means for fastening the first and second wearing members 340a and 340b.

A body housing 330 of the body part 310 may have a shape including the curvature. Since the seat part 321 is formed with the elastic material and elastically deformed, the seat part 321 may be coupled to the body part 310 while being deformed to be suitable for the shape of the body part 310. When the wearing part 320 has a changeable structure, the wearing part 320 may be implemented in various designs or colors. For example, the wearing part 320 may be used as an accessory showing the individuality of the user.

Referring to FIG. 3B, the body part 310 has a curvature. The front surface F of the body housing 330 has the display 311 disposed thereon to allow the user to conveniently view the displayed screen. The rear surface (R) of the body housing 330 has the sensor module 210 (for example, the vital signal measurement sensor) disposed thereon, so as to closely contact the wrist of the user's body.

The body housing 330 may have a proper curvature in consideration of a user's body shape, for example, a thickness or a curvature of the wrist. The sensor unit 210 included in the body part 310 may include at least one of the photo sensor, the GSR sensor, the temperature sensor, and the heartbeat sensor. Although the display 311 has a shape reflecting the user's body curve as an example, the display 311 may be implemented by a flat LCD or OLED display, a curved display, or a flexible display.

The sensor unit 210 includes a sensor interface unit 360, e.g., an interface window, disposed on the rear surface R of the body part 310. The sensor interface unit 360 may be disposed on a protrusion unit so that the sensor unit 210 may more closely contact the user's body when detecting the vital signal. Connection members 350, for example, charging terminals, are also arranged on the rear surface R of the body part 310. The connection members 350 may be disposed close to the sensor unit 210.

Referring to FIG. 3C, the sensor unit 210 includes the acceleration sensor 221 and vital sensors for measuring vital signal, for example, the heart rate sensor 234, the GSR sensor 232, and the temperature sensor 233. The sensor unit may be disposed on the rear surface R of the body part 310 or at a predetermined location of the wearing part 320, which closely contacts the user.

According to an embodiment of the present invention, the acceleration sensor 221 may be a biaxial (x and y axes) acceleration sensor or a triaxial (x, y, and z axes) acceleration sensor. The sensor unit 210 may measure various vital signals of the human body and output various vital sensor values related to the human body, and at least one of the vital sensors may be activated to detect a wearing state. According to an embodiment of the present invention, in order to detect the wearing state, the heart rate sensor 234 may be activated, the GRS sensor 232 may be activated, or the temperature sensor 233 may be activated. Alternatively, two or more sensors may be activated. In addition to the aforementioned sensors, other vital sensors for detecting a sensing value may be included to determine the wearing state.

Figure 4A:
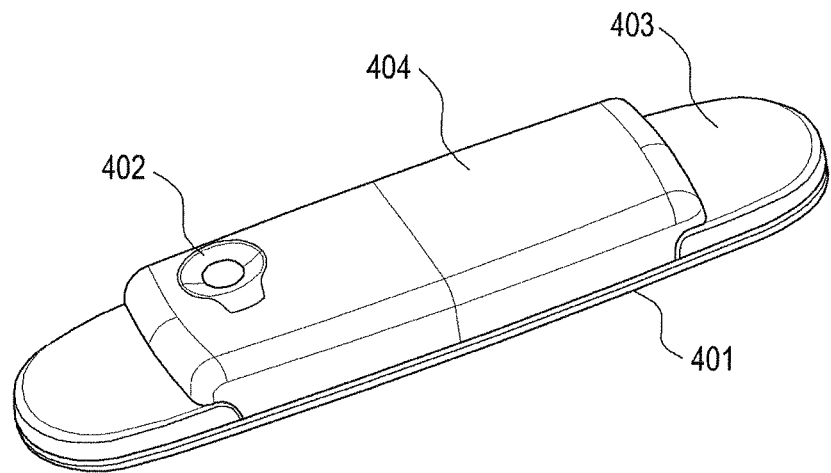
FIG. 4A is a diagram illustrating a patch type electronic device that measures a vital signal, according to an embodiment of the present invention.
Figure 4B:
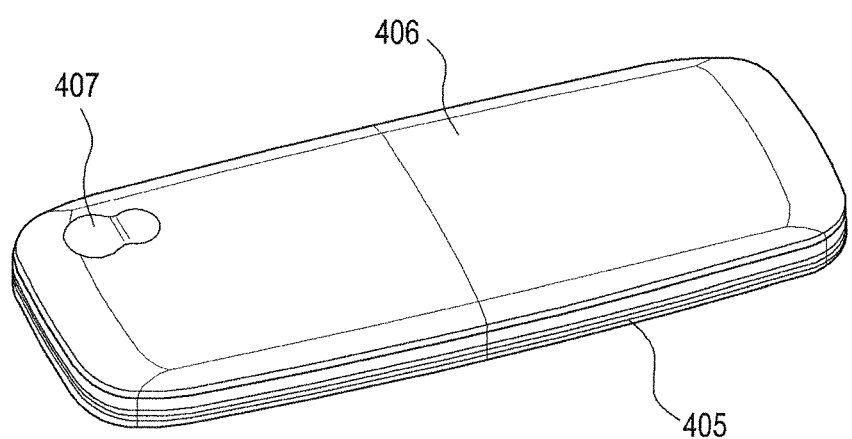
FIG. 4B is a diagram illustrating a patch type electronic device that measures a vital signal, according to another embodiment of the present invention.
Figure 4C:
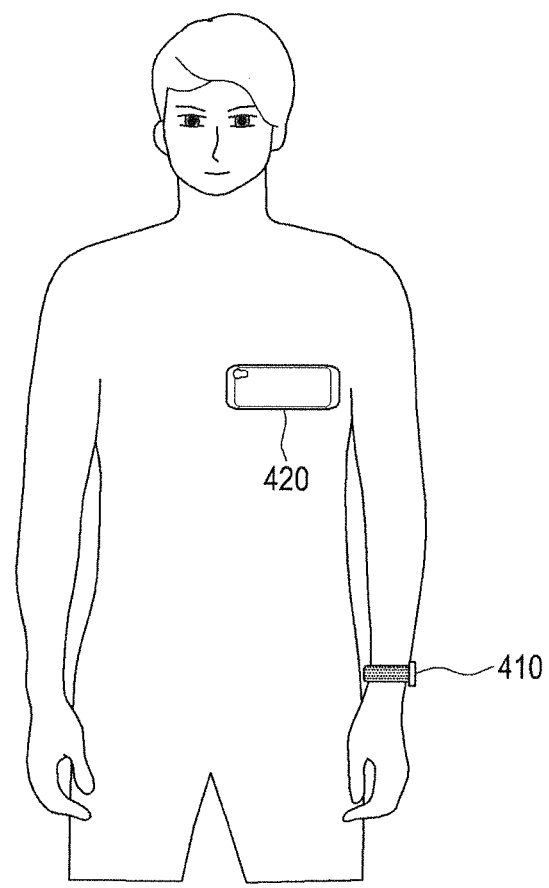
FIG. 4C is a diagram illustrating an electronic device mounted on a body part (chest or wrist), according to an embodiment of the present invention.
Figure 4D:
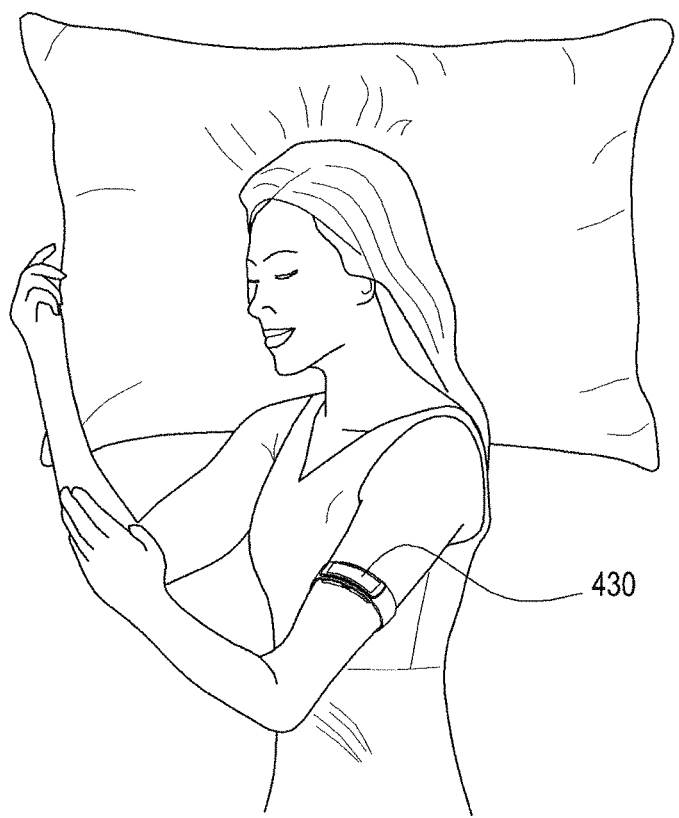
FIG. 4D is a diagram illustrating an electronic device worn on a wrist, according to an embodiment of the present invention.
Figure 4E:
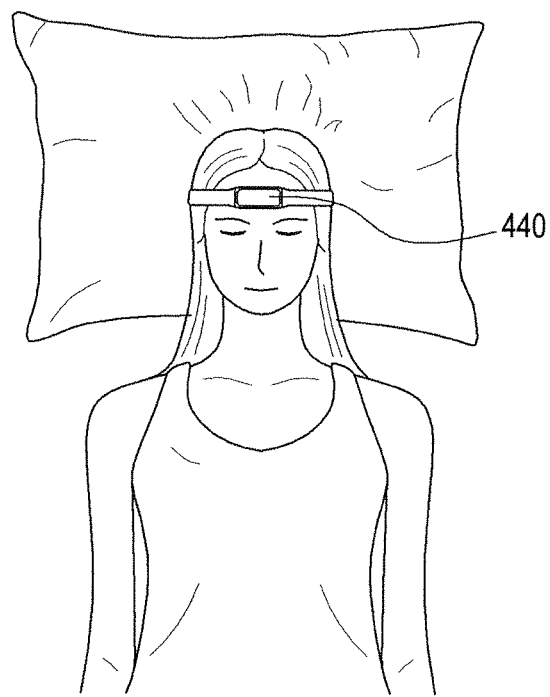
FIG. 4E is a diagram illustrating an electronic device worn on the forehead, according to an embodiment of the present invention.
Figure 4F:
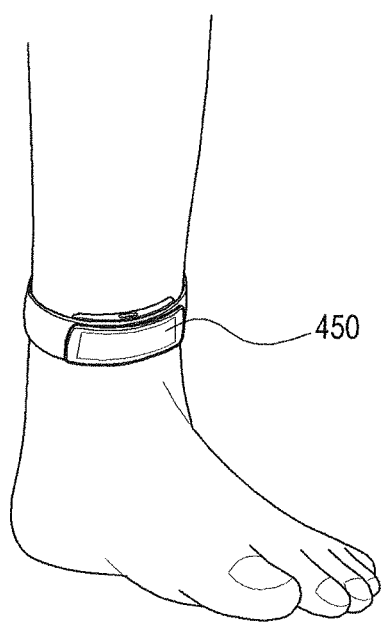
FIG. 4F is a diagram illustrating an electronic device worn on the ankle, according to an embodiment of the present invention.

FIG. 4A is a diagram illustrating a patch type electronic device that measures a vital signal, according to an embodiment of the present invention. FIG. 4B is a diagram illustrating a patch type electronic device that measures a vital signal, according to another embodiment of the present invention. FIG. 4C is a diagram illustrating an electronic device mounted on a body part, according to an embodiment of the present invention. FIG. 4D is a diagram illustrating an electronic device worn on the wrist, according to an embodiment of the present invention. FIG. 4E is a diagram illustrating an electronic device worn on the forehead, according to an embodiment of the present invention. FIG. 4F is a diagram illustrating an electronic device is worn on the ankle, according to an embodiment of the present invention.

The electronic device 101, according to an embodiment of the present invention, may include a wearable (or patch type) electronic device having at least one sensor for measuring a vital signal of the user, and the electronic device 101 or at least one sensor may be mounted on a body part. Further, the electronic device 101, according to an embodiment of the present invention, may receive a vital signal measured by at least one sensor, analyze a received parameter, and convert the analyzed parameter into vital information. At least one sensor may be mounted on the body while being structurally separated from the electronic device, and the electronic device 101 may include various electronic devices such as a portable terminal, a mobile phone, a notebook, and a tablet PC, which can be carried by the user.

Referring to FIG. 4A, a patch type electronic device 404 is integrally configured with an adhesive part 401 to be attached to the skin of the human body, and a pad 403 flexibly bent along a curved surface of the human body when attached. The electronic device 404 may be attached to a particular part of the human body through the adhesive part 401 and, even when the surface of the human body is bent, maintain adhesion due to the pad 403. Further, the exterior of the electronic device 404 includes a switch 402 for controlling the operation of the electronic device 404. The switch 402 may control an ON/OFF operation of the electronic device 404. Further, a hole for measuring the vital signal may be formed on the adhesive part 401, and the electronic device 404 may measure the vital signal through the hole. The patch type electronic device 404 may transmit the measured vital signal to the electronic device 101.

Referring to FIG. 4B, a patch type electronic device 406, according to another embodiment of the present invention, is integrally configured with an adhesive part 405 for attachment to the skin of the human body. Further, the exterior of the electronic device 406 includes a switch 407 for controlling the operation of the electronic device 406. In addition, a hole for measuring the vital signal may be formed on the adhesive part 405, and the electronic device 406 may measure the vital signal through the hole. The patch type electronic device 406 may transmit the measured vital signal to the electronic device 101. The exteriors, size, and designs of the patch type electronic devices of FIGS. 4A and 4B may be freely changed to easily measure the vital signal and may vary depending on a desired attachment location on the human body.

Referring to FIG. 4C, the user may wear an electronic device 410 (for example, a smart watch) including at least one sensor on the wrist. Further, the electronic device 410 may receive the measured vital signal from a patch type electronic device 420 (for example, a heart rate measuring device) attached to the chest. The electronic devices 410 and 420 may include a sensor for measuring the vital signal. The electronic devices 410 and 420 may transmit the measured vital signal to various electronic devices, such as, for example, a portable terminal, a mobile phone, a notebook, or a tablet PC of the user. Alternatively, the electronic devices 410 and 420 may transmit vital information acquired using the measured vital signal to various electronic devices, such as, for example, a portable terminal, a mobile phone, a notebook, or a tablet PC of the user.

Referring to FIG. 4D, the electronic device 101 is embodied as an arm band 430 which can be worn on the arm. The arm band 430 may calculate a motion strength within a predetermined time and determine a change in the motion strength. When a pattern of the change in the motion strength corresponds to a predetermined pattern, the arm band 430 may determine whether the arm band 430 is worn on the arm. When the arm band 430 is worn on the arm, the arm band 430 may monitor sleep.

Referring to FIG. 4E, the electronic device 101 may be embodied as a hair band 440 which can be worn on the head. The hair band 440 may calculate a motion strength within a predetermined time and determine a change in the motion strength. When a pattern of the change in the motion strength corresponds to a predetermined pattern, the hair band 440 may determine whether the hair band 440 is worn on the head. When the hair band 440 is worn on the head, the hair band 440 may monitor sleep.

Referring to FIG. 4F, the electronic device 101 may be embodied as an anklet 450 which can be worn on the ankle. The anklet 450 may calculate a motion strength within a predetermined time and determine a change in the motion strength. When a pattern of the change in the motion strength corresponds to a predetermined pattern, the anklet 450 may determine whether the anklet 450 is worn on the ankle. When the anklet 450 is worn on the ankle, the anklet 450 may monitor sleep. According to an embodiment of the present invention, various electronic devices may be mounted on any body part of the user from which the vital signal of the user can be measured.

At least one of the electronic devices 101, 404, 406, 410, 420, 430, 440, and 450 may detect a motion to measure the vital signal and, when the motion is smaller than a predetermined threshold, measure the vital signal. At least one of the electronic devices 101, 404, 406, 410, 420, 430, 440, and 450 may detect a motion, and include at least one of the acceleration sensor, photo sensor, GSR sensor, temperature sensor, and heart rate sensor, which may measure the vital signal.

Figure 5:
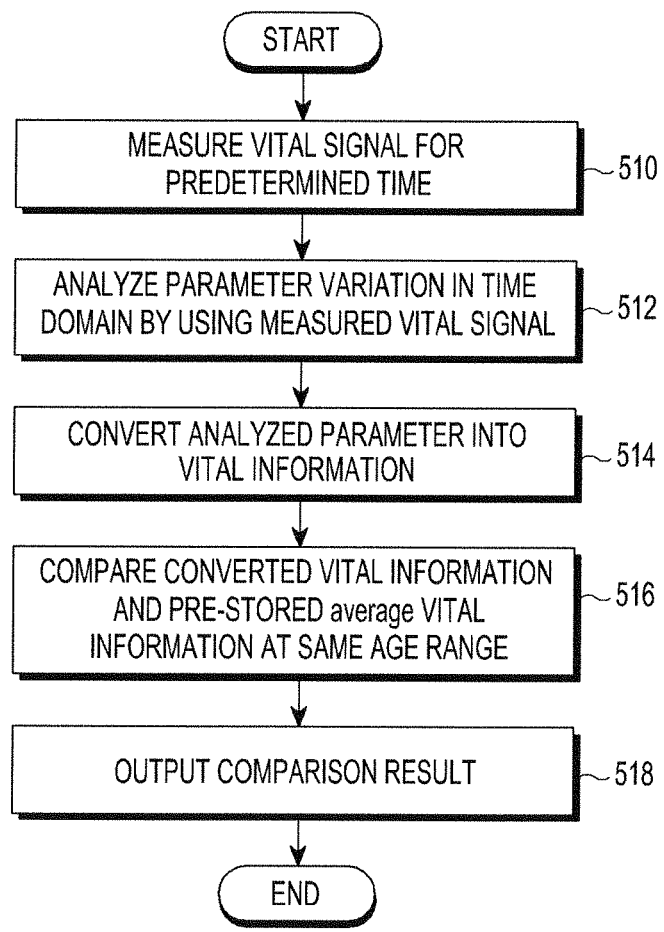
FIG. 5 is a flowchart illustrating a method of measuring a vital signal, according to an embodiment of the present invention.

FIG. 5 is a flowchart illustrating a method of measuring a vital signal, according to an embodiment of the present invention.

The electronic device 101 measures the vital signal for a predetermined time, in step 510. The electronic device 101 may measure the vital signal at least one time. The electronic device 101 may measure the vital signal for a predetermined time (for example, 30 seconds) at least one time. The predetermined time may be in units of seconds or minutes. The measurement may be made in units of milliseconds ms. The predetermined time and the time of the measurement unit (for example, ms) may be variably controlled.

The measurement time based on the parameter of the vital signal, according to an embodiment of the present invention, is shown in Table 1 below.

TABLE 1

| HRV variables | Length (s) | Correlation | p-value |
|---|---|---|---|
| HR | 10 | 0.9321 | 0.5879 |
| SDNN | 240 | 0.9866 | 0.1280 |
| RMSSD | 30 | 0.7716 | 0.0905 |
| pNN50 | 60 | 0.9168 | 0.1278 |
| LF | 90 | 0.8636 | 0.0975 |
| HF | 20 | 0.6709 | 0.1863 |
| TF | 240 | 0.9989 | 0.0971 |
| VLF | 270 | 0.9997 | 0.2663 |
| nLF | 90 | 0.8452 | 0.6357 |
| nHF | 90 | 0.8452 | 0.6357 |
| LF/HF | 90 | 0.8151 | 0.6357 |

Table 1 shows a correlation and a p-value between values acquired through analysis based on standard 5 minutes and a minimum analysis time determined with respect to parameters in a time domain, such as, for example, HR, SDNN, RMSSD, and pNN50, and parameters in a frequency domain, such as, for example, low-frequency (LF), high-frequency (HF), time-frequency (TF), very low-frequency (VLF), normalized low-frequency (nLF), normalized high-frequency (nHF), and low-frequency/high-frequency (LF/HF), through a Kruskal-Wallis test The Kruskal-Wallis test corresponds to a method of arranging data between two different groups in a size order, deciding orders, and then testing the data by using an average of the orders. When the Kruskal-Wallis test is performed, the p-value is output, which is a reference of determining correctness of a null hypothesis. In the null hypothesis, there is generally a conditional difference in a resulting difference between two compared sample groups. Alternatively, a hypothesis that the two sample groups do not belong to the same population is set.

The null hypothesis may be dismissed when the p-value is very small. For example, in order to show that two groups are meaningfully different (that is there is a meaningful difference between averages of the two groups), a condition of p-value <0.05 or p-value <0.01 is generally used. When the p-value meets the condition, the null hypothesis is dismissed. Since the p-values of the parameters of the time domain such as, for example, HR, SDNN, RMSSD, and pNN50, and the parameters of the frequency domain, such as, for example, LF, HF, TF, VLF, nLF, nHF, and LF/HF, do not meet the condition p-value <0.05 or p-value <0.01, the null hypothesis indicating that the two groups are meaningfully different is dismissed. Accordingly, it is noted that there is no statistically meaningful difference between the measured value of each parameter for a corresponding time and the measured value for 5 minutes.

The correlation indicates a linearity level between two groups, or whether two groups have a linearity relation therebetween. When a value measured by one group increases, and a value measured by the other group also increases, positive linearity exists. In contrast, when a value measured by one group increases, and a value measured by the other group decreases, negative linearity exists. The correlation shows the linearity level. FIGS. 17A, 17B, and 17C illustrate the correlation for each age range between a result of analysis of each parameter in the time domain and each parameter in the frequency domain based on data of different lengths and a result of analysis of the parameters based on standard 5-minute length data, and illustrate results of measuring the parameters of Table 1 according to each age range for each of various durations of time.

As shown in Table 1, in a case of the time domain parameters HR, SDNN, RMSSD, and pNN50, data lengths of 10 seconds, 240 seconds, 30 seconds, and 60 seconds have statistically similar values to those of 5-minute data. In general, SDNN is related to stress and RMSSD has a high correlation with SDNN. Accordingly, the vital signal can be sufficiently measured without distortion by using RMSSD requiring 30 seconds instead of SDNN requiring 240 seconds. Further, since unconscious and continuous vital signal measurement can be performed in the wearable device, SDNN can be used.

The electronic device 101 analyzes the variation of the parameter in the time domain by using the measured vital signal, in step 512. The electronic device 101 converts the analyzed parameter into vital information, in step 514. The electronic device 101 may measure the vital signal at least one time and analyze the parameter of the measured vital signal. The electronic device 101 may analyze the parameter in a time domain of the measured vital signal and analyze a variation of the parameter by using an interval between beats of the vital signal. The HR corresponding to the parameter in the time domain may be a square root of an average value of values generated by raising differences of continuous RR intervals, and the measurement time may be in units of seconds. In this case, the electronic device 101 may accumulate measured RR intervals and measure and accumulate the RR intervals until a final sum thereof exceeds a predetermined time. Further, the electronic device 101 may measure and accumulate the RR intervals until the number of heartbeats reaches a predetermined threshold. The vital signal may include at least one of a heartbeat, a pulse, an impedance plethysmography, a BCG, an ECG, a PPG, and a blood flow rate. The parameters may include at least one of an HR, an RR interval, an SDNN, an RMSSD, and a pNN50. The heartbeat interval may include at least one of the RR interval, the pulse interval, and the JJ interval of the vital signal. The RR interval refers to an interval between two peaks of the ECG, the JJ interval refers to an interval between two peaks of the BCG, and the pulse interval refers to the PPG and an interval between two peaks of the PPG.

The electronic device 101 may convert the parameter into the vital information by taking the natural logarithm (ln) of a reciprocal of the parameter. The electronic device 101 may convert the analyzed parameter into the vital information by using Equation (1) below.

$$\ln(1000/P) \qquad (1)$$

In Equation (1), P denotes a parameter.

The electronic device 101 compares the converted vital information, e.g., stress index, with a pre-stored average vital information, e.g., stress index, at the same age range and output a result of the comparison, in steps 516 and 518. The electronic device 101 may compare the converted stress index with a stress index at the same age range as that of the user. The average stress index may be pre-stored in the electronic device 101 or received from the server 106. Through the comparison, it may be determined whether the stress index of the user of which the vital signal is measured is higher or lower than the average stress index at the same age or the same age range.

When the converted stress index is higher than the stress index at the same age range, the electronic device 101 may generate and output a guide to reduce the stress index. When the converted stress index is lower than the stress index at the same age range, the electronic device 101 may generate and output a guide indicating that the stress index is low and including information useful for health. The guide may include at least one of information to reduce the stress index, an alarm informing that the stress index is high, and a breathing method to reduce the stress index. The electronic device 101 may output the comparison result and/or the generated guide through at least one of a sound, a vibration, and a GUI. The electronic device 101 may detect a breathing quantity or receive information on whether breathing is detected through at least one sensor included in the sensor module 1840 and information on the breathing rate to determine that the breathing is detected and analyze the breathing rate. When breathing is detected from the user while the guide is output, the electronic device 101 may compare the detected breathing with the guide in real time and output a result thereof.

Figure 6A:
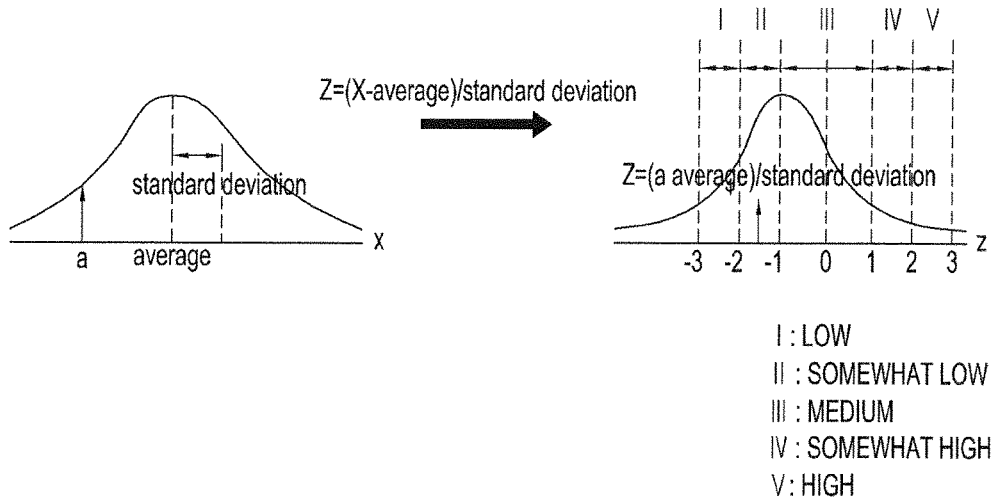
FIG. 6A is a diagram illustrating a comparison between a user's stress index and an average stress index at the same age range, according to an embodiment of the present invention.
Figure 6B:
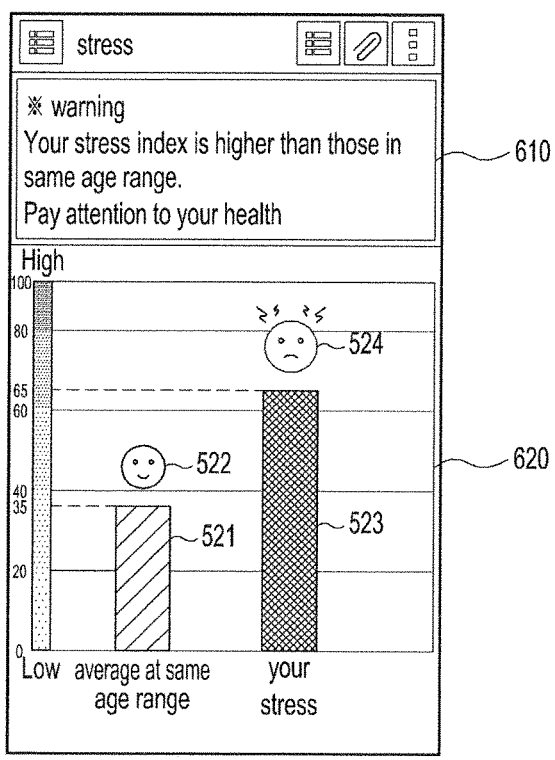
FIG. 6B is a diagram illustrating a comparison result when the user's stress index is higher than the average stress index at the same age range, according to an embodiment of the present invention.

FIG. 6A is a diagram illustrating a comparison of the user's stress index and an average stress index at the same age range, according to an embodiment of the present invention. FIG. 6B is a diagram illustrating a user's stress index that is higher than the average stress index at the same age range, according to an embodiment of the present invention.

Referring to FIG. 6A, an average and a deviation of parameters of a plurality of people are calculated according to each age range, and the measured parameters of the user are converted into stress indexes based on the average and the deviation at the same age range. The stress indexes are divided into a plurality of sections according to a level how much higher or lower the stress index of the user is than the stress index at the same age range. Accordingly, the user may identify how much higher or lower the user's stress index is. A first section represents a case where the user's stress index is significantly lower than the average stress index at the same age range. A second section represents a case where the user's stress index is a little lower than the average stress index at the same age range. A third section represents a case where the user's stress index is a little higher than the average stress index at the same age range. A fourth section represents a case where the user's stress index is a moderately higher than the average stress index at the same age range. A fifth section represents a case where the user's stress index is significantly higher than the average stress index at the same age range. Through the comparison, the user is able to determine how much higher or lower his/her own stress index is than stress indexes of other people at the same age range, and a result of the comparison may be output through the display 150.

Referring to FIG. 6B, when the user's stress index is higher than the average stress index at the same age range, the electronic device 101 outputs the comparison result through the display 150. According to the comparison result, the display 150 may display information for reducing the stress index when the user's stress index is higher than the stress index at the same age range. The display 150 may be divided into a first area 610 for displaying information indicating that the stress index is high or low and information useful for health, and a second area 620 for displaying how much higher or lower the user's stress is than the average stress index in the same age range.

For example, when the user's stress index is higher than the stress index at the same age range, the first area 610 displays a warning message to instruct the user to pay attention to his/her health since the stress index is higher than the stress index at the same age range. The first area 610 may also display various pieces of information such as, for example, foods, an exercise method, a weight control method, and a breathing method to reduce the stress index. Further, the first area 610 may display an animation to instruct the user to pay attention to his/her health since the stress index is higher than the stress index at the same age range. The second area 620 displays a graph 523 corresponding to the user's stress index and a graph 521 corresponding to the average stress index at the same age range. Further, according to a difference between the user's stress index and the stress index at the same age range, the second area 620 may display emoticons with different facial expressions 522 and 524, and the user may recognize the seriousness in reducing the user's stress through the facial expressions of the emoticons.

Figure 7:
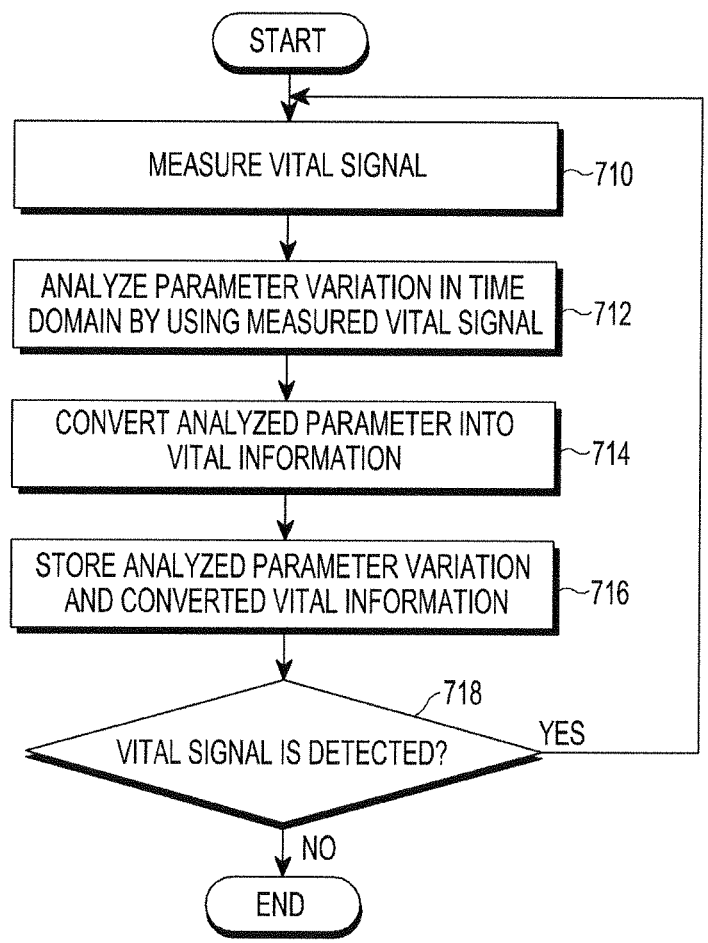
FIG. 7 is a flowchart illustrating a process of measuring a vital signal and storing a stress index in accordance with the measured vital signal, according to an embodiment of the present invention.

FIG. 7 is a flowchart illustrating a process of measuring a vital signal and storing a stress index in accordance with the measured vital signal, according to an embodiment of the present invention.

The electronic device 101 measures a vital signal, in step 710, as described above with respect to FIG. 5.

The electronic device 101 analyzes a parameter variation in the time domain by using the measured vital signal, in step 712. The electronic device converts the analyzed parameter into vital information, in step 714, as described above with respect to FIG. 5.

The electronic device 101 stores the analyzed parameter variation and the converted vital information, in step 716, as described above with respect to FIG. 5.

In step 178, the electronic device 101 determines whether the vital signal is detected. When the vital signal is detected, the electronic device 101 returns to step 710 and measures the vital signal. Steps 710 to 718 are repeatedly performed for a predetermined time or while the vital signal is detected.

Figure 8:
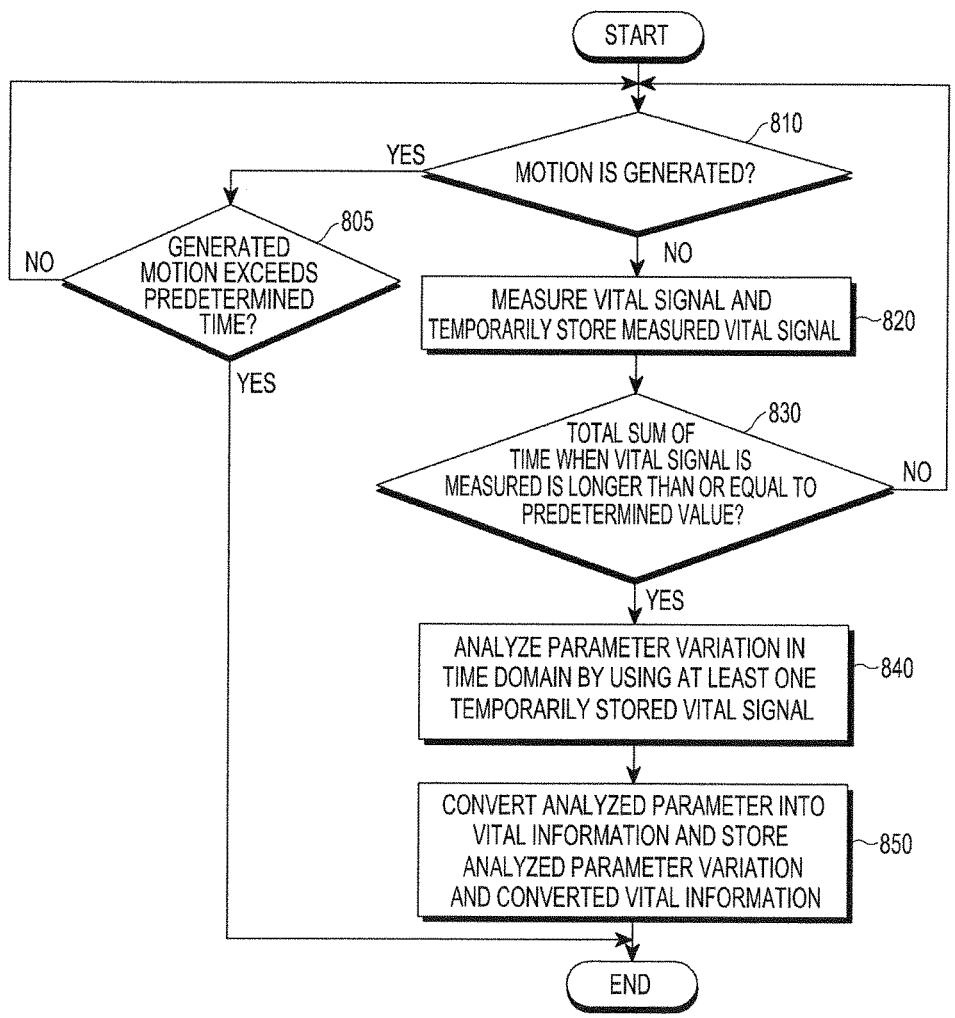
FIG. 8 is a flowchart illustrating a process of combining vital signals to convert the vital signal into vital information, according to an embodiment of the present invention.

FIG. 8 is a flowchart illustrating a process of combining vital signals to convert the vital signal into vital information, according to an embodiment of the present invention.

Referring to FIG. 8, in step 810, it is determined whether motion is generated. When no motion is generated, the electronic device 101 measures the vital signal and temporarily stores the measured vital signal, in step 820. When motion is detected, the electronic device 101 determines whether the generated motion lasts longer than a predetermined time. When the generated motion does not last as long as the predetermined time, the electronic device 101 returns to step 810 to detect whether the motion is generated. When the generated motion lasts as long as or longer than the predetermined time, the methodology terminates.

In step 830, the electronic device determines whether a total sum of times when a vital signal is measured is longer than or equal to a predetermined value. When a total sum of measurement times is larger than or equal to a predetermined value, the electronic device 101 analyzes a parameter variation in the time domain by using at least one temporarily stored vital signal, in step 840. The electronic device 101 may add stored vital signals and analyze the parameter variation in the time domain by using the added vital signals.

The electronic device 101 may convert the analyzed parameter into vital information and store the analyzed parameter variation and the converted vital information, in step 850.

When it is determined the total sum of measurement times is smaller than the predetermined value in step 830, the electronic device 101 returns to step 310 determine whether motion is generated.

Figure 9A:
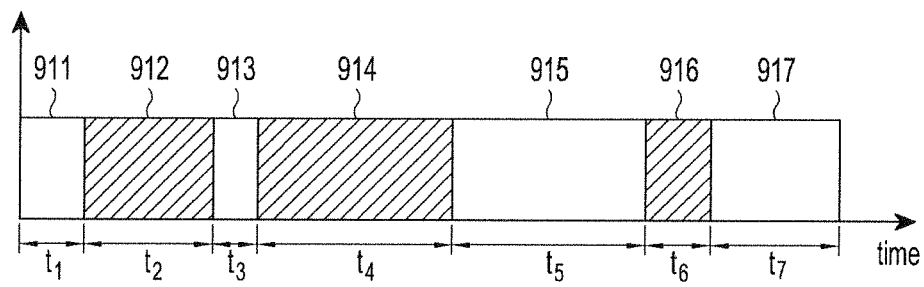
FIG. 9A is a diagram illustrating sections in which a vital signal is measured, according to an embodiment of the present invention.
Figure 9B:
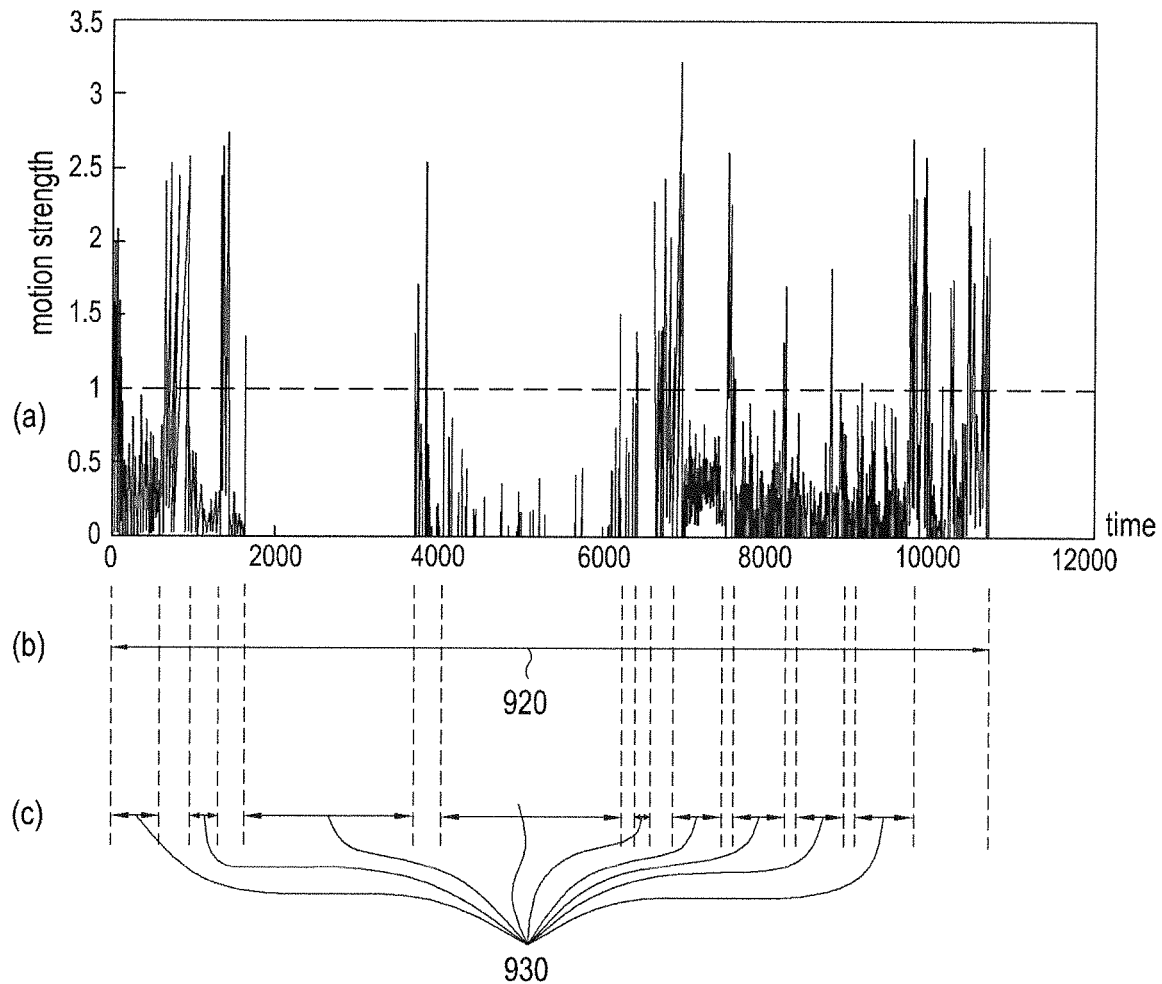
FIG. 9B is a diagram illustrating a motion strength, according to an embodiment of the present invention.
Figure 9C:
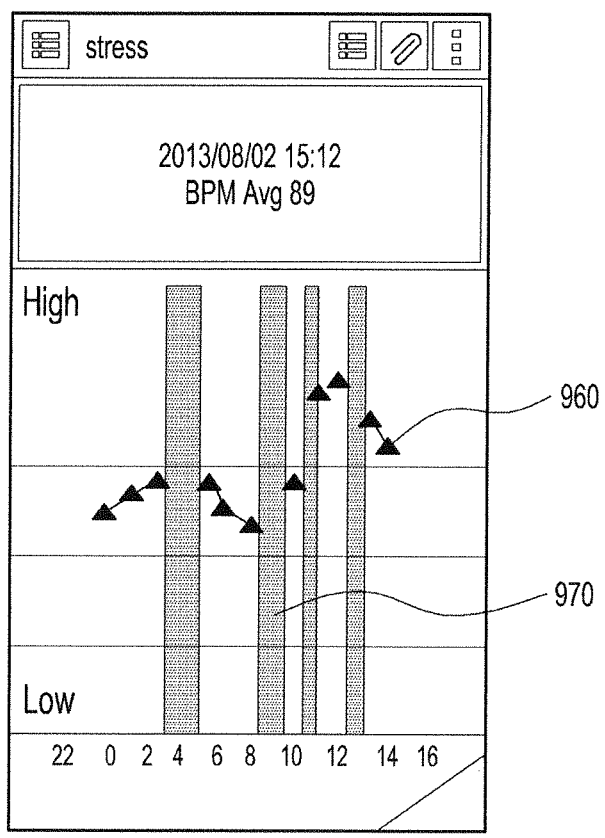
FIG. 9C is a diagram illustrating a change in stress measured for one day, according to an embodiment of the present invention.

FIG. 9A is a diagram illustrating a section in which the vital signal is measured, according to an embodiment of the present invention. FIG. 9B is a diagram illustrating a motion strength, according to an embodiment of the present invention. FIG. 9C is a diagram illustrating an aspect of a change in stress measured for one day, according to an embodiment of the present invention.

Referring to FIG. 9A, the electronic device 101 measures the vital signal while no motion is generated. When the motion is generated, the electronic device 101 temporarily stops measuring the vital signal. A first section 911, a third section 913, a fifth section 915, and a seventh section 917 correspond to sections in which the vital signal is measured, and a second section 912, a fourth section 914, and a sixth section 916 correspond to sections in which the vital signal is not measured. The first section 911 is a section in which the vital signal is measured for a first time (t1), the third section 913 is a section in which the vital signal is measured for a third time (t3), the fifth section 915 is a section in which the vital signal is measured for a fifth time (t5), and the seventh section 917 is a section in which the vital signal is measured for a seventh time (t7). Similarly, the second section 912 is a section in which no vital signal is measured for a second time (t2), the fourth section 914 is a section in which no vital signal is measured for a fourth time (t4), and the sixth section 916 is a section in which no vital signal is measured for a sixth time (t6).

When a total sum of the time of the sections in which the vital signal is measured (for example, the first, third, fifth, and seventh sections) is longer than a predetermined time (for example, 30 seconds), the electronic device 101 may combine the vital signals measured in the first section 911, the third section 913, the fifth section 915, and the seventh section 917 and analyze the parameter variation in the time domain by using the combined vital signal. When the motion of the electronic device 101 is continuously generated for a predetermined time (for example, 1 minute) or longer in a state where the total sum of the time of the sections in which the vital signal is measured is shorter than the predetermined time (for example, 30 seconds), the electronic device 101 may not use the vital signal, which is measured before the motion is generated, for combing the vital signals.

Referring to FIG. 9B, a horizontal (X) axis corresponds to a time axis and a vertical (Y) axis corresponds to a motion strength axis. graph segment (a) illustrates a motion strength according to the time, graph segment (b) illustrates a section in which the sensor module is activated according to a conventional predetermined time period, and graph section (c) illustrates a section in which the sensor module is activated when the motion strength is smaller than a predetermined threshold (for example, smaller than 1), according to an embodiment of the present invention. Through a comparison between graph segments (b) and (c), the sensor module is activated according to a predetermined time period 920 but the sensor module is activated only when the motion strength is smaller than a predetermined threshold (for example, smaller than 1), as indicated by reference numeral 930. Accordingly, the sensor module is activated only when needed, thereby reducing battery consumption.

Referring to FIG. 9C, the electronic device 101 measures the vital signal while no motion is generated. When the motion is generated, the electronic device 101 temporarily stops measuring the vital signal. When no motion is generated after the temporarily stop, the electronic device 101 measures the vital signal again. When no motion is generated or the motion is smaller than a predetermined threshold, the electronic device 101 measures the vital signal to determine stress, and the stress may be shown by a graph 960 according to the measurement time. The electronic device 101 may display a section 970 in which the vital signal is not measured together with the graph 960.

Figure 10:
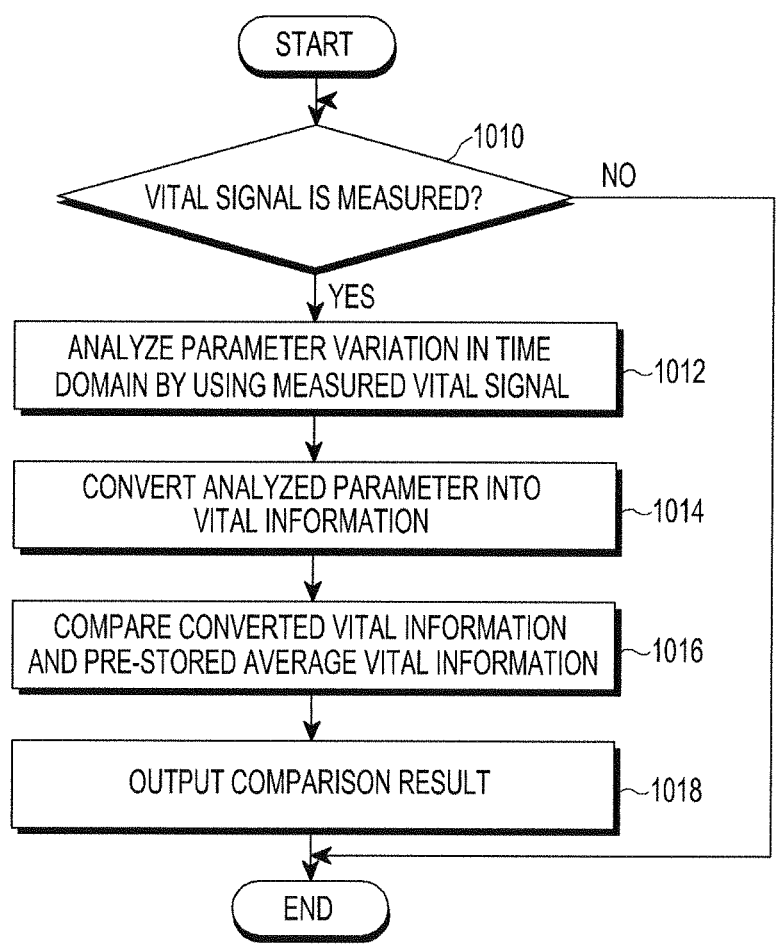
FIG. 10 is a flowchart illustrating a process of comparing a current stress index and an average stress index of the user, according to an embodiment of the present invention.

FIG. 10 is a flowchart illustrating a process of comparing a current stress index and an average stress index of the user, according to an embodiment of the present invention.

Referring to FIG. 10, in step 1010, it is determined whether a vital signal is measure. When the vital signal is not measured, the methodology terminates. When the vital signal is measured, the electronic device 101 analyzes a parameter variation in the time domain by using the measured vital signal, in step 1012. The electronic device converts the analyzed parameter into vital information (for example, the stress index), in step 1014.

The electronic device 101 compares the converted stress index and the pre-stored average stress index, in step 1016. The electronic device 101 may compare the stress index and the user's average stress index pre-stored in the storage unit 130. The electronic device 101 may compare the user's current stress index and the user's average stress index pre-stored in the storage unit 130 in response to the measurement of the vital signal. The storage unit 130 may store the converted stress index in accordance with the vital signal measured by the user in real time under a control of the electronic device 101. The storage unit 130 may calculate an average of the converted stress indexes in accordance with the vital signal measured by the user in the unit of at least one of time zones, dates, days of the week, months, and years and store the calculated average under a control of the electronic device 101. The storage unit 130 may calculate an average of a plurality of pre-stored stress indexes in the unit of at least one of time zones, dates, days of the week, months, and years and store the calculated average under a control of the electronic device 101. Further, the storage unit 130 may store the average stress index for each age range (for example, teens, twenties, thirties . . . ), periodically or aperiodically receive the average stress index from the server 106, and store the received average stress index.

The electronic device 101 outputs a result of the comparison, in step 1018. Further, when the converted stress index is higher than the pre-stored stress index, the electronic device 101 may generate a guide to reduce the stress index. When the converted stress index is lower than the pre-stored stress index, the electronic device 101 may generate a guide indicating that the stress index is low and including information useful for health.

Figure 11A:
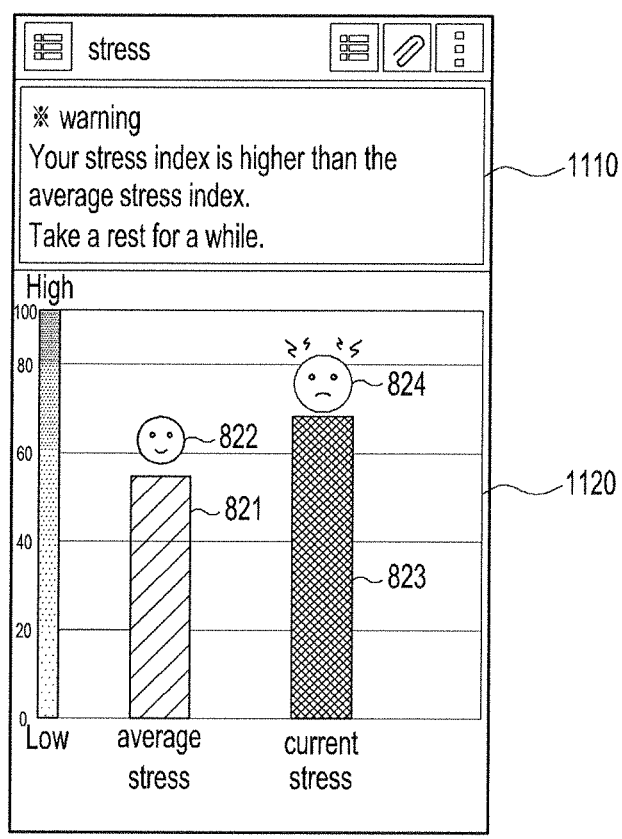
FIG. 11A is a diagram illustrating a comparison between the current stress index of the user and a pre-stored average stress index, according to an embodiment of the present invention.
Figure 11B:
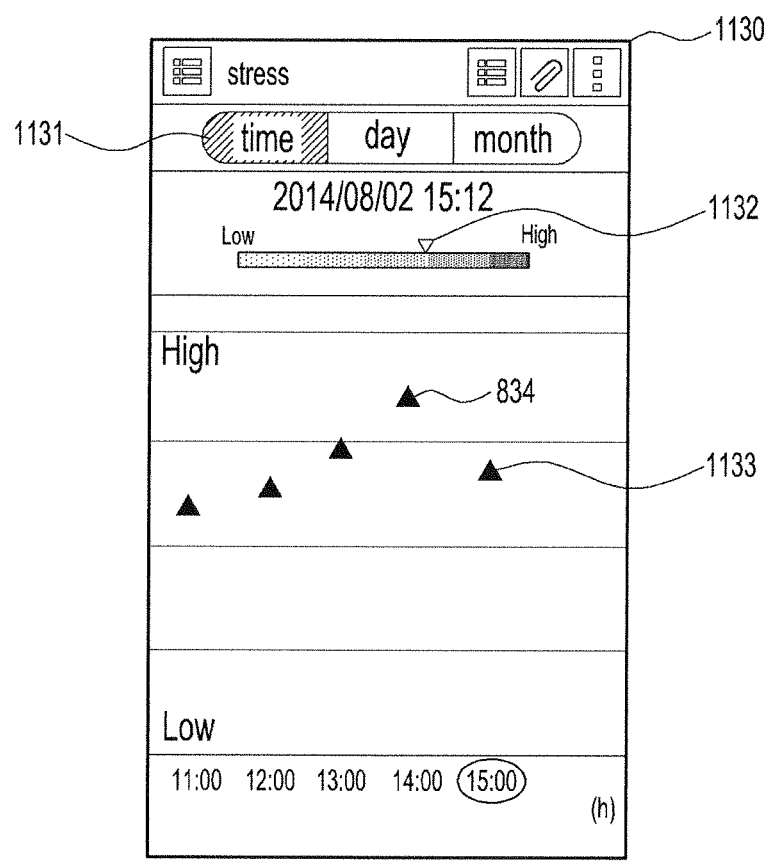
FIG. 11B is a diagram illustrating an average stress index of the user based on each time zone, according to an embodiment of the present invention.
Figure 11C:
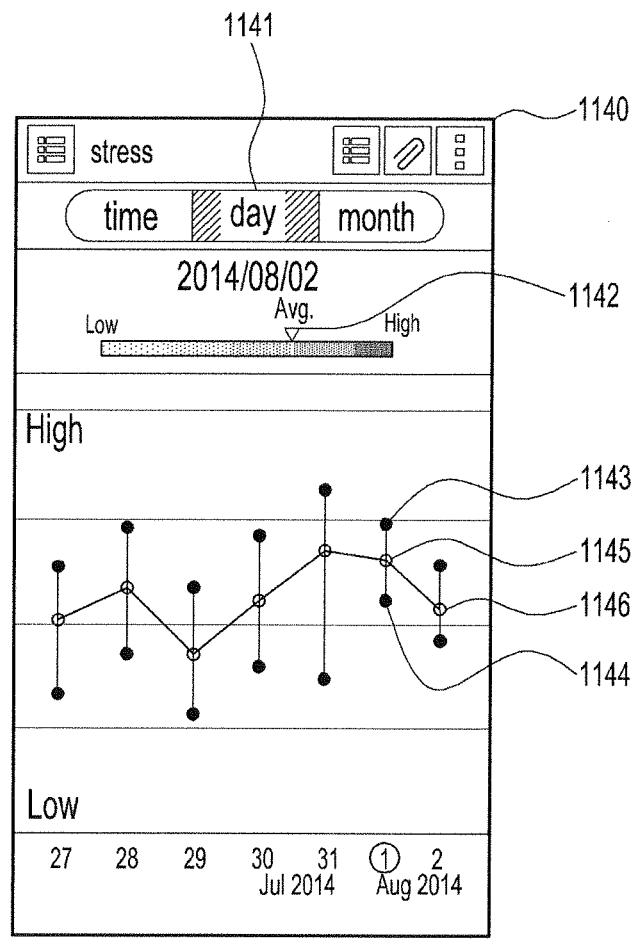
FIG. 11C is a diagram illustrating a comparison between a current stress index and an average stress index based on the date, according to an embodiment of the present invention.
Figure 11D:
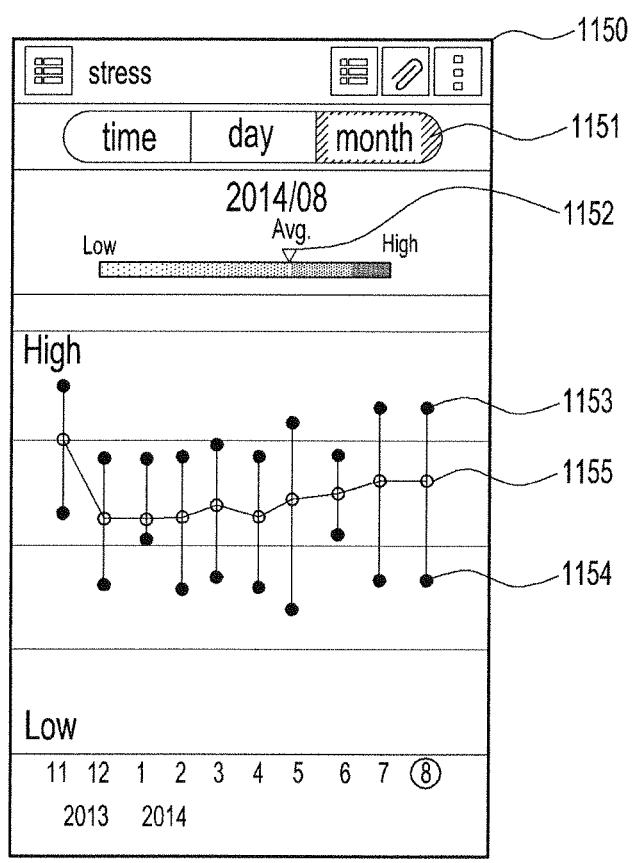
FIG. 11D is a diagram illustrating a comparison between a current stress index and an average stress index based on the month, according to an embodiment of the present invention.
Figure 11E:
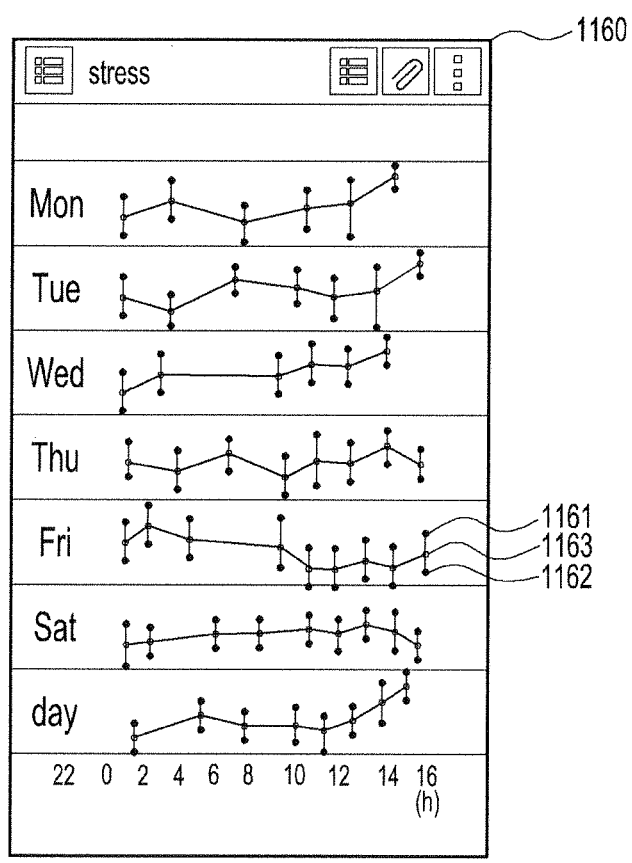
FIG. 11E is a diagram illustrating a comparison between a current stress index and an average stress index based on the day of the week, according to an embodiment of the present invention.
Figure 11F:
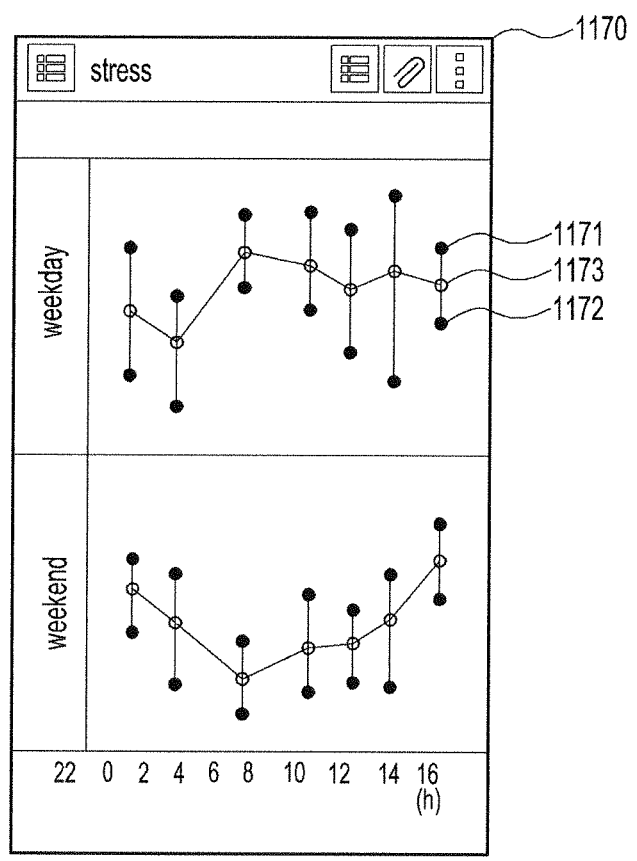
FIG. 11F is a diagram illustrating a comparison between a current stress index and an average stress index based on the weekday and the weekend, according to an embodiment of the present invention.
Figure 11G:
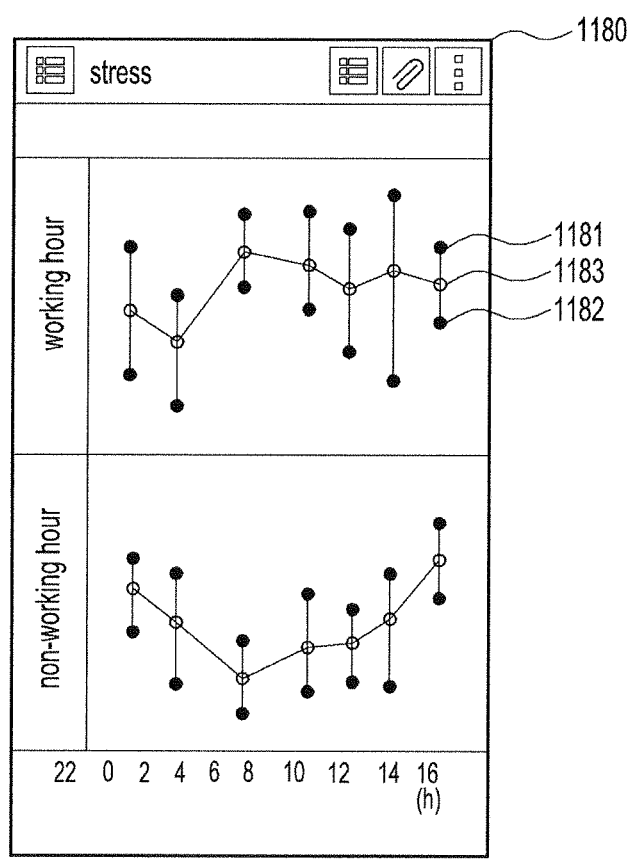
FIG. 11G is a diagram illustrating a comparison between a current stress index and an average stress index based on working hours and the non-working hours, according to an embodiment of the present invention.

FIG. 11A is a diagram illustrating a comparison between the user's current stress index and the pre-stored average stress index, according to an embodiment of the present invention. FIG. 11B is a diagram illustrating the average stress index of the user at each time zone, according to an embodiment of the present invention. FIG. 11C is a diagram illustrating a comparison between the current stress index and the average stress index based on each date, according to an embodiment of the present invention. FIG. 11D is a diagram illustrating a comparison between the current stress index and the average stress index based on each month, according to an embodiment of the present invention. FIG. 11E is a diagram illustrating a comparison between the current stress index and the average stress index based on each day of the week, according to an embodiment of the present invention. FIG. 11F is a diagram illustrating a comparison between the current stress index and the average stress index based on the weekday and the weekend, according to an embodiment of the present invention. FIG. 11G is a diagram illustrating a comparison between the current stress index and the average stress index based on working hours and non-working hours, according to an embodiment of the present invention.

Referring to FIG. 11A, when the user's stress index is higher or lower than the pre-stored average stress index, the electronic device 101 outputs a result of the comparison through the display 150. According to the comparison result, the display 150 is divided into a first area 1110 for displaying information indicating that the stress index is high or low and information useful for health, and a second area 1120 for displaying how much higher or lower the user's stress is than the average stress index at the same age range.

For example, when the user's stress index is higher than the pre-stored stress index, the first area 1110 displays a warning message to instruct the user to pay attention to his/her health since the stress index is higher than the average stress index previously measured and calculated, and may display various pieces of information such as, for example, foods, an exercise method, a weight control method, and a breathing method to reduce the stress index. Further, the first area 1110 may display an animation to instruct the user to pay attention to his/her health since the stress index is higher than the average stress index. The second area 1120 may display a graph 823 corresponding to the user's current stress index and a graph 821 corresponding to the pre-stored average stress index. Further, according to a difference between the user's stress index and the pre-stored average stress index, the second area 1120 may display emoticons with different facial expressions 822 and 824, and the user may recognize the seriousness in reducing the stress through the facial expressions of the emoticons.

Referring to FIG. 11B, the electronic device 101 displays a stress index averaged according to each time segment 1131 on a display 1130. For example, when today is Aug. 2, 2014, the electronic device 101 may calculate an average of stress indexes according to each time segment on August 2, and display the calculated average on the display 1130 in units of time. For example, the electronic device 101 displays an average of a plurality of stress indexes measured by the user at time segments from 14:00 to 15:00 as a point 834, and the user may recognize the time segment at which the stress index is high. When the current time is 15:12, the point 1133 indicating the current stress index may change in real time according to a real time change in the stress index. When it becomes 16:00, the electronic device 101 may calculate an average of stress indexes measured for one hour from 15:00, and display the average on the display 1130 like the point 834. Point 1132 shows a level of the current stress index compared to a maximum value and a minimum value at the same time.

Referring to FIG. 11C, the electronic device 101 displays a stress index averaged according to each day 1141 on a display 1140. For example, when this month is August, 2014, the electronic device 101 calculates an average of stress indexes according to each date in August, and displays the calculated average according to each date on the display 1140. For example, the electronic device 101 displays a maximum value and a minimum value of the stress index measured according to each date as points, and the user may recognize the date on which the stress index is high or low. For example, when displaying the stress index on August 1, the electronic device may display a point 1143 indicating a maximum stress index and a point 1144 indicating a minimum stress index, so that the user may recognize a stress change amount on August 1 and compare the stress index with a stress index on another date. A point indicating the current stress index may also change in real time according to a real time change in the stress index. An average stress index on August 1 is displayed as a point 1145. When today is August 2, the electronic device 101 displays a maximum stress index and a minimum stress index measured on (August 2, and calculates an average of the stress indexes measured during today and display a point 1146 on the display 1140. A point 1142 shows a level of the average stress index on current date. Further, a point may change in real time according to a real time change in the stress index.

Referring to FIG. 11D, the electronic device 101 displays a stress index averaged according to each month 1151 on a display 1150. For example, when this year is 2014, the electronic device 101 calculates an average of stress indexes according to each month of 2014, and displays the calculated average according to each month on the display 1150. For example, the electronic device 101 displays a maximum value and a minimum value of the stress index measured according to each month as points, and the user may recognize the month in which the stress index is high or low. For example, when displaying the stress index on August, the electronic device 101 displays a point 1153 indicating a maximum stress index and a point 1154 indicating a minimum stress index. When the current month is August, a point indicating the current stress index may change in real time according to a real time change in the stress index. An average stress index on August may be displayed as a point 1155. A point 1152 shows a level of the average stress index on current month.

Referring to FIG. 11E, the electronic device 101 displays a stress index averaged according to each day of the week on a display 1160. The electronic device 101 calculates an average of the stress indexes according to each day of the week and each time of day and displays the calculated average on the display 1160 according to each day of the week and each time of day.

The electronic device 101 displays a maximum value and a minimum value of the stress index measured according to each day of the week as points, and the user may recognize the day of the week on which the stress index is high or low. For example, when displaying the stress index on Friday, the electronic device 101 displays a point 1161 indicating a maximum stress index at 4 p.m. on Friday and a point 1162 indicating a minimum stress index at 4 p.m. on Friday, so that the user may recognize a stress change amount on Friday and compare the stress index with a stress index on another day of the week. An average stress index at 4 p.m. on Friday may be displayed as a point 1163.

Referring to FIG. 11F, the electronic device 101 displays a stress index averaged according to weekdays and the weekend on a display 1170. In general, the weekdays refer to Monday to Friday, and the weekend refers to Saturday and Sunday. The electronic device 101 calculates averages of the stress indexes of the weekdays and the weekend by times on those days and displays the calculated averages on the display 1170.

The electronic device 101 may display a maximum value and a minimum value of the stress index measured according to the weekdays and the weekend as points, and the user may recognize which one between the weekdays and the weekend has a high stress index or a low stress index. For example, when displaying the stress index at 4 p.m. on weekdays, the electronic device 101 displays a point 1171 indicating a maximum stress index and a point 1172 indicating a minimum stress index, so that the user may recognize a stress change amount on weekdays and compare the stress index with a stress index on the weekend. An average stress index at 4 p.m. on weekdays may be displayed as a point 1173.

Referring to FIG. 11G, the electronic device 101 displays stress indexes averaged according to working hours and non-working hours on a display 1180. In general, working hours correspond to 9 a.m. to 6 p.m., and non-working hours correspond to the time other than the working hours. The electronic device 101 calculates averages of the stress indexes of the working hours and the non-working hours and displays the calculated averages on the display 1180. The working hours and the non-working hours may be variably controlled.

The electronic device 101 displays a maximum value and a minimum value of the stress index measured according to the working hours and the non-working hours as points, and the user may recognize which one between the working hours and the non-working hours has a high stress index or a low stress index. For example, when displaying the stress index of the working hours, the electronic device 101 displays a point 1181 indicating a maximum stress index at 4:00 p.m. during the working hours and a point 1182 indicating a minimum stress index at 4 p.m. during the working hours, so that the user may recognize a stress change amount during working hours and compare the stress index with a stress index during non-working hours. An average stress index at 4:00 p.m. of the working hours may be displayed as a point 1183.

Figure 12:
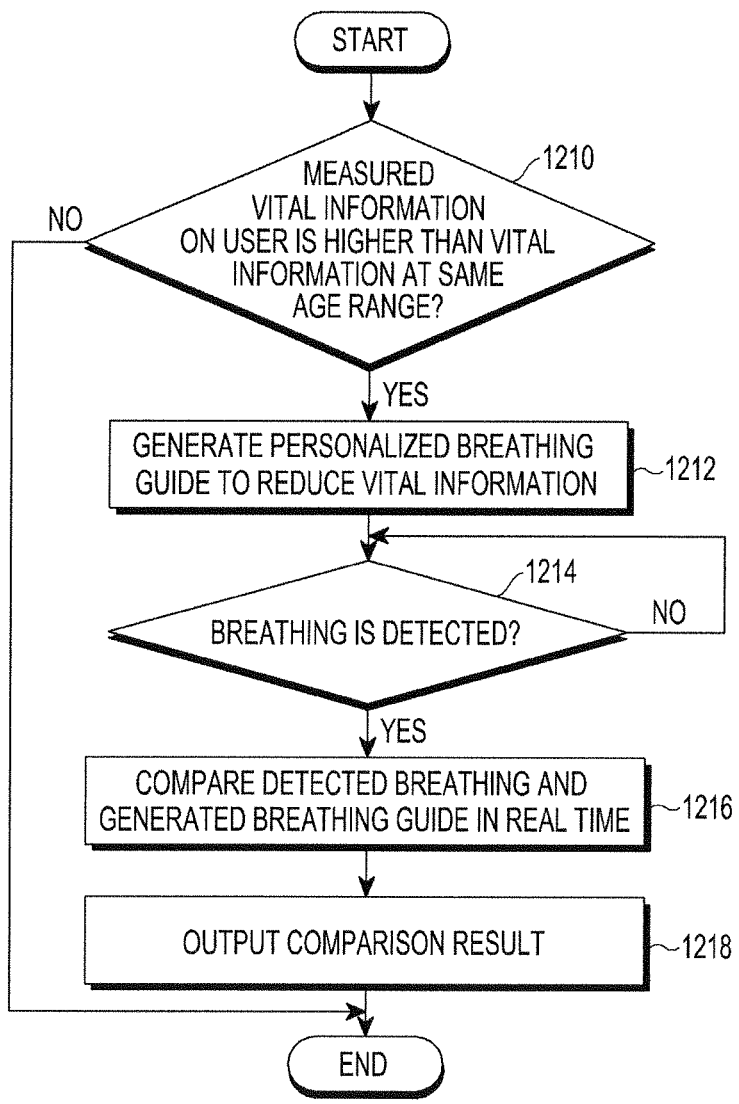
FIG. 12 is a flowchart illustrating a process for outputting a personalized breathing guide to reduce stress when stress is high, and outputting a result of a comparison between actual breathing and the guide, according to an embodiment of the present invention.

FIG. 12 is a flowchart illustrating a process for outputting a personalized breathing guide to reduce stress when the stress is high, and outputting a result of a comparison between actual breathing and the guide, according to an embodiment of the present invention.

In step 1210, the electronic device 101 determines whether measured vital information for user is higher than vital information at a same age range. When the measured user's vital information, e.g., stress index, is higher than the stress index at the same age range, the electronic device 101 generates a breathing guide for reducing the stress index, in step 1212. A process for measuring the vital signal, converting the measured vital signal into the vital information, and comparing the converted vital information with the average vital information at the same age range is the same as described above.

In step 1214, the electronic device 101 determines whether breathing is detected. When the breathing is detected, the electronic device 101 compares the detected breathing with the generated breathing guide in real time, in step 1216, and outputs a result of the comparison, in step 1218. The electronic device 101 may detect breathing or receive information on whether there is breathing detected through at least one sensor included in a sensor module and information on a breathing rate to determine that the breathing is detected and analyze the breathing quantity. The electronic device 101 may output the generated guide and the stress index varying according to real time breathing. The electronic device 101 may output the comparison result and/or the generated guide through at least one of a sound, a vibration, and a GUI.

Figure 13:
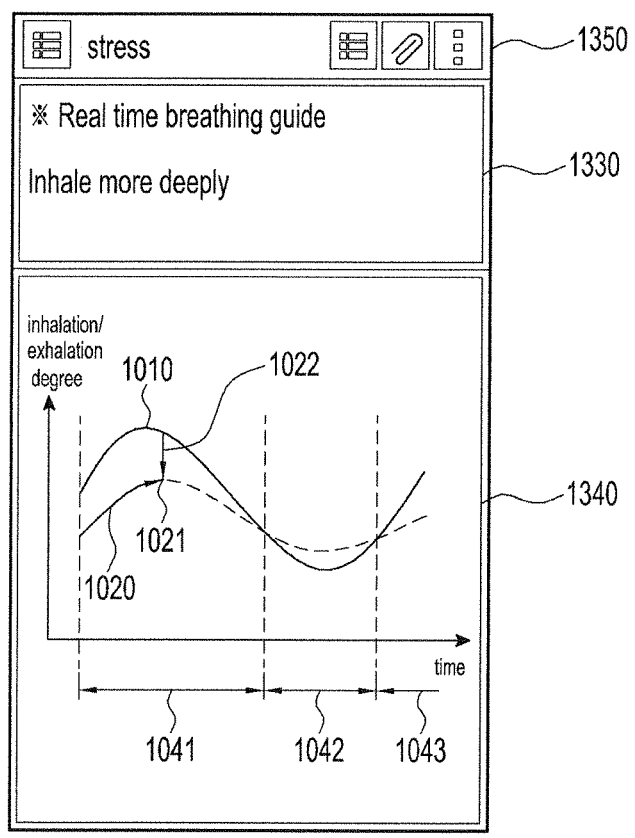
FIG. 13 is a diagram illustrating real time breathing for reducing the stress index when guide is output, according to an embodiment of the present invention.

FIG. 13 is a diagram illustrating real time breathing for reducing the stress index in a state where the guide is output, according to an embodiment of the present invention.

Referring to FIG. 13, when the user's stress index is higher than the average stress index at the same age range, the electronic device 101 outputs various pieces of information and the stress index varying due to the breathing to reduce the stress index in real time through the display 1350. The electronic device 101 divides the display 1350 into a first area 1330 for displaying useful information for reducing the stress index and a second area 1340 for outputting a user's breathing rate to reach the average stress index at the same age range in real time. When the user's stress index is higher than the stress index at the same age range, the display 1350 displays information for reducing the stress index under a control of the electronic device 101. For example, when the user's stress index is higher than the stress index at the same age range, the display 1350 outputs information instructing the user to inhale more deeply to reduce the stress index in the first area 1330, and outputs the stress index varying according to the degree of inhalation and exhalation in the second area 1340, in real time. The first area 1330 may display a warning message instructing the user to pay attention to his/her health and display an animation. The second area 1340 displays a breathing guide curve 1010 for reaching the stress index at the same age range and a real time breathing curve 1020 showing a breathing rate of current breathing 1021 of the user to reach the breathing guide curve. The second area 1340 displays a guide showing that a character the breaths as the user breathes, or expresses inhalation and exhalation through a scene in which a balloon expands/contracts or a scene in which a dolphin sinks and then rises. Further, the electronic device 101, according to an embodiment of the present invention may output a person's voice containing a comment that guides inhalation and exhalation, or may apply pressure to the user's skin according to the user's inhalation and exhalation through a tactile sensor included in the sensor module 1840. The curve of the real time breathing curved line 1020 before the current breathing 1021 may be expressed by the solid line. For example, the second area 1340 is divided into a first section 1041, a second section 1042, and a third section 1043 according to the breathing time. A case where an inhalation quantity is smaller than the inhalation quantity proposed by the breathing guide corresponds to the first section 1041, a case where an exhalation quantity is smaller than the exhalation quantity proposed by the breathing guide corresponds to the second section 1042, and a case where the inhalation quantity is smaller than the inhalation quantity proposed by the breathing guide corresponds to the third section 1043. The second area 1340 displays, as a value, a difference 1022 between the inhalation quantity proposed by the breathing guide and an inhalation quantity of current breathing 1021 in the first section 1041. According to the difference 1022 between the inhalation quantity proposed by the breathing guide and the inhalation quantity of the current breathing, information displayed in the first area may vary. For example, when the inhalation quantity proposed by the breathing guide is different from the current inhalation quantity, the first area displays "inhale more deeply". Further, when the exhalation quantity proposed by the breathing guide is different from the current exhalation quantity, the first area may display "exhale more deeply".

Figure 14:
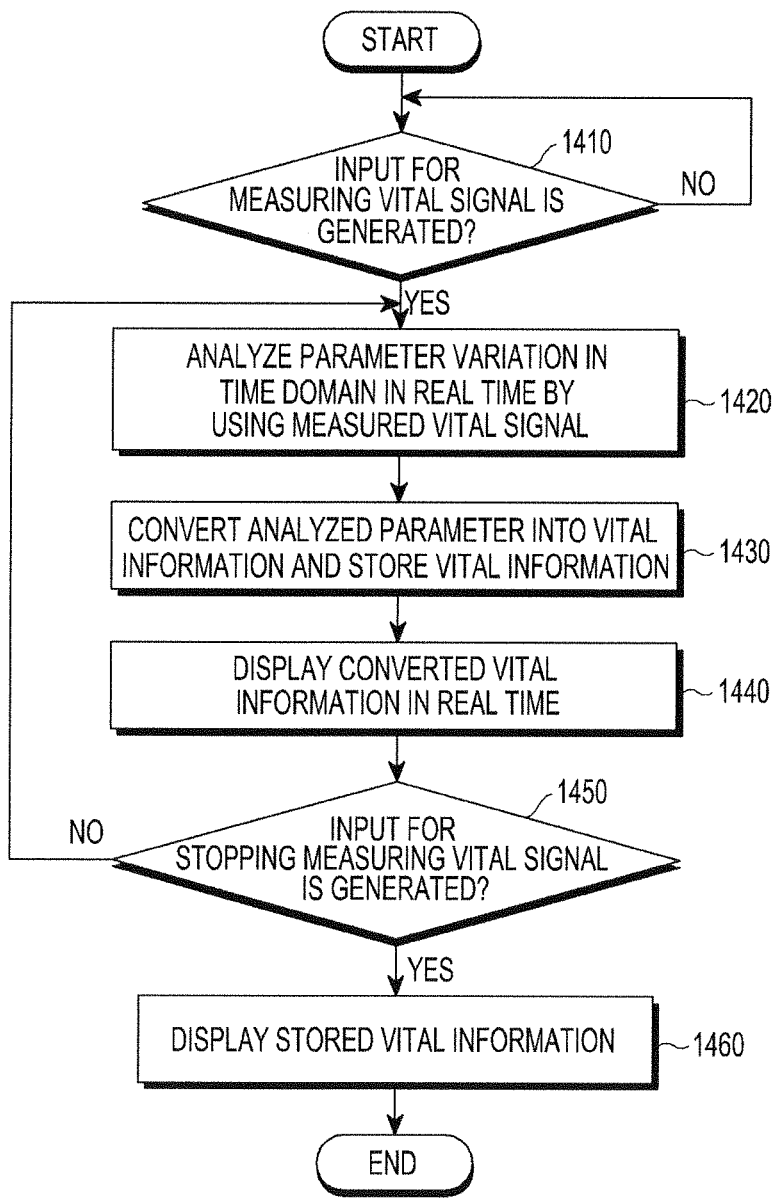
FIG. 14 is a flowchart illustrating a method of measuring a vital signal, according to another embodiment of the present invention.

FIG. 14 is a flowchart illustrating a method of measuring a vital signal, according to another embodiment of the present disclosure.

In step 1410, the electronic device determines whether an input for measuring a vital signal is generated. When an input for measuring the vital signal is generated, the electronic device 101 analyzes a parameter variation in the time domain in real time by using the measured vital signal, in step 1420. The electronic device 101 may analyze the parameter variation by using an interval between beats of the measured vital signal. For example, when the user desires to know a change in the stress index of the user for a predetermined time, such as while watching a movie or a soap opera, or going to a concert, the electronic device 101 starts measuring the vital signal in response to the input.

The electronic device 101 converts the analyzed parameter into vital information and stores the vital information, in step 1430. The electronic device 101 displays the converted stress index in real time. in step 1440. The electronic device 101 may display the stored stress index on the display 150.

In step 1450, it is determined whether an input for stopping measurement of the vital signal is generated. When the input for stopping measurement of the vital signal is detected, the electronic device 101 stops measuring the vital signal and displays the stress index stored in step 1430 on the display 150, in step 1460. For example, when the user desires to know a change in the stress index through the vital signal measured for a predetermined time, such as while watching a movie or a soap opera, the electronic device 101 may display the stress index stored in step 1430 on the display 150 in the form of a graph in response to the input. Accordingly, the user may know the section in which the stress index increases or decreases for the predetermined time.

When it is determined that an input for stopping measurement of the vital signal is not generated in step 1450, the electronic device returns to step 1420.

Figure 15A:
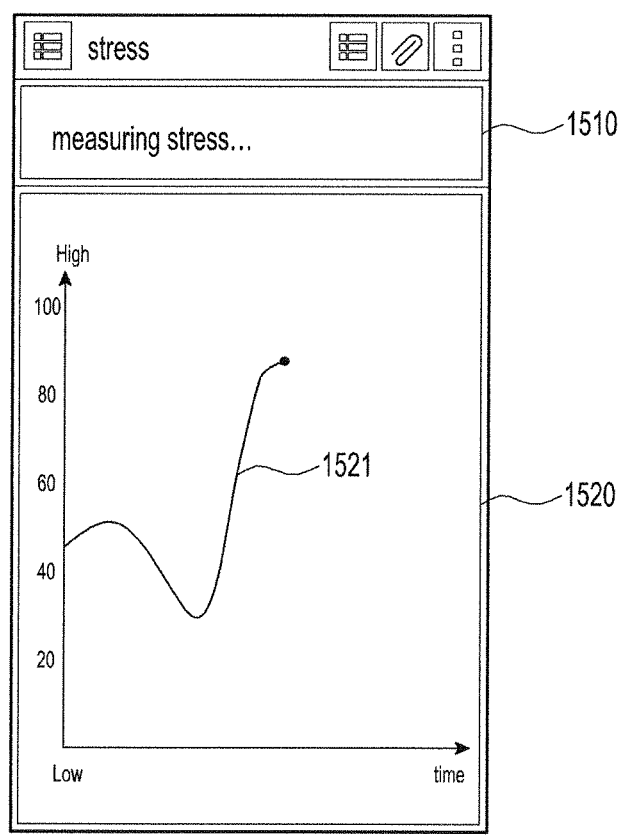
FIG. 15A is a diagram illustrating the displaying of a stress index in real time according to measurement of the vital signal, according to an embodiment of the present invention.
Figure 15B:
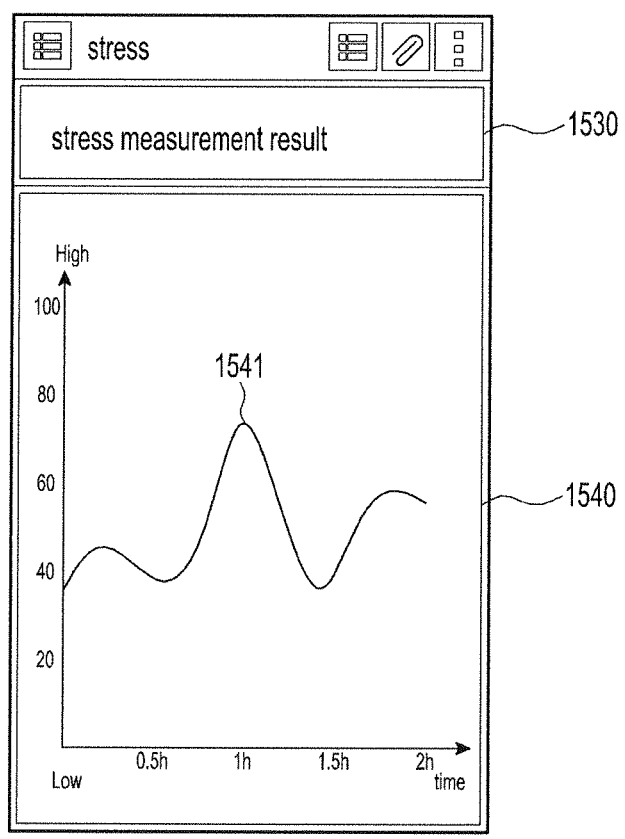
FIG. 15B is a diagram illustrating the displaying of a stress index corresponding to a vital signal measured for a predetermined time, according to an embodiment of the present invention.

FIG. 15A is a diagram illustrating the displaying of the stress index in real time according to the measurement of the vital signal, according to an embodiment of the present invention. FIG. 15B is diagram illustrating the displaying of the stress index corresponding to the vital signal measured for a predetermined time, according to an embodiment of the present invention.

Referring to FIG. 15A, the electronic device 101 displays the stress index on the display 150 in real time according to the measurement of the vital signal. The electronic device 101 may display information indicating that the stress is currently measured in a first area 1510, and the trend of the change in the stress index 1521 in a second area 1520. Accordingly, the user may recognize the trend 1521 of the current stress index of the user. For example, when the user desires to know a change in the stress index of the user for a predetermined time, such as while watching a movie or a soap opera, or going to a concert, the electronic device 101 may start measuring the vital signal in response to an input and display the stress index corresponding to the measured vital signal on the display 150 in real time.

Referring to FIG. 15B, the electronic device 101 displays the stored stress index on the display 150 according to the measurement of the vital signal. The electronic device 101 may store the stress index converted through the measured vital signal according to the measurement of the vital signal. In the measurement of the vital signal, storing the stress index may be repeatedly performed for a predetermined time. The electronic device 101 displays information informing of a stress measurement result in a first area 1530 and the stored stress index in a second area 1540 in response to the detection of the input for stopping measuring the vital signal. Accordingly, the user may view a trend 1541 of the stress index of the user for the predetermined time. For example, when the user desires to know the change in the stress index of the user for a predetermined time, such as while watching a movie or a soap opera or going to a concert, the electronic device 101 may display the stress index corresponding to the vital signal measured for the predetermined time (for example, 2 hours) on the display 150.

Figure 16A:
FIG. 16A is a graph illustrating an ECG of a vital signal, according to an embodiment of the present invention.
Figure 16B:
FIG. 16B is a graph illustrating a BCG of a vital signal, according to an embodiment of the present invention.
Figure 16C:
FIG. 16C is a graph illustrating a PPG of a vital signal, according to an embodiment of the present invention.

FIG. 16A is a graph illustrating an ECG of the vital signal, according to an embodiment of the present invention. FIG. 16B is a graph illustrating a BCG of the vital signal, according to an embodiment of the present invention. FIG.

Figure 16D:
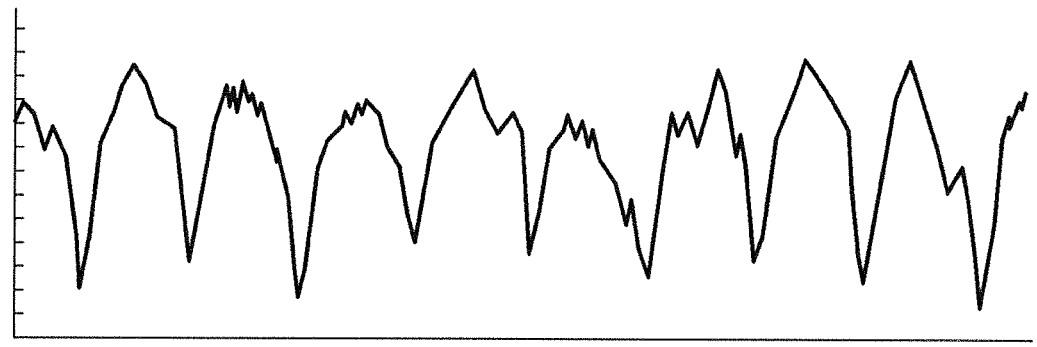
FIG. 16D is a graph illustrating an impedance plethysmography of a vital signal, according to an embodiment of the present invention.
Figure 16E:
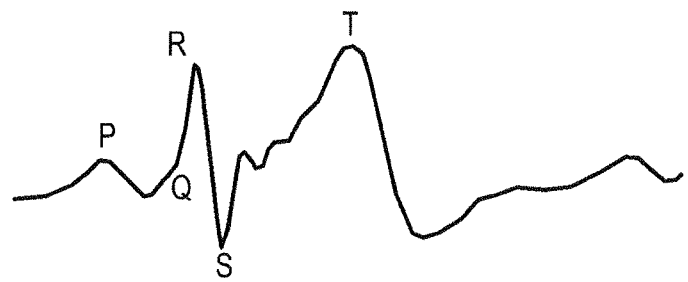
FIG. 16E is a graph illustrating an RR interval of an ECG, according to an embodiment of the present invention.
Figure 16F:
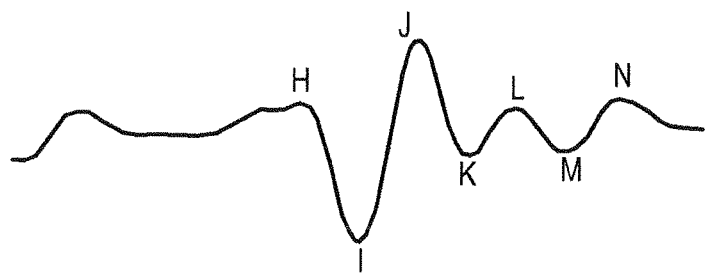
FIG. 16F is a graph illustrating a JJ interval of a BCG, according to an embodiment of the present invention.

16C is a graph illustrating a PPG of the vital signal, according to an embodiment of the present invention. FIG. 16D is a graph illustrating an impedance plethysmography of the vital signal, according to an embodiment of the present invention. FIG. 16E is a graph illustrating an RR interval of the ECG, according to an embodiment of the present invention. FIG. 16F is a graph illustrating a JJ interval of the BCG, according to an embodiment of the present invention.

The vital signal, according to an embodiment of the present invention, may include at least one of a heart rate, a pulse, an impedance plethysmography, a BCG, an ECG, a PPG, and a blood flow rate. The present disclosure may include various vital signals used for measuring the user's stress index as well as the aforementioned vital signal. Parameters analyzed through the vital signal may include at least one of a HR, an RR interval, SDNN, RMSSD, and pNN50. The heart rate interval may include at least one of the RR interval, the pulse interval, and the JJ interval of the vital signal. The RR interval refers to an interval between two peaks of the ECG, the JJ interval refers to an interval between two peaks of the BCG, and the pulse interval refers to an interval between peaks of the impedance plethysmography and the PPG.

FIG. 17A is a chart showing a correlation for each age range between a result of analysis of parameters in the time domain based on standard 5-minute length data and a result of analysis of the parameters based on data of different lengths, according to an embodiment of the present invention. FIGS. 17B and 17C are charts showing a correlation for each age range between a result of analysis of parameters in the frequency domain based on standard 5-minute length data and a result of analysis of the parameters based on data of different lengths, according to an embodiment of the present invention.

FIGS. 17A, 17B, and 17C illustrate results of Table 1, which shows the correlation between HRV parameters calculated through the conventional standard 5-minute and the measurement time, according to an embodiment of the present invention, according to each age range and each of various time zones for the parameters in the time domain and the parameters in the frequency domain. As illustrated in FIGS. 17A, 17B, and 17C, the correlation indicates whether the linearity exits, and decreases with respect to all age ranges and the HRV parameter as the measurement time of the RR interval decreases.

Figure 18:
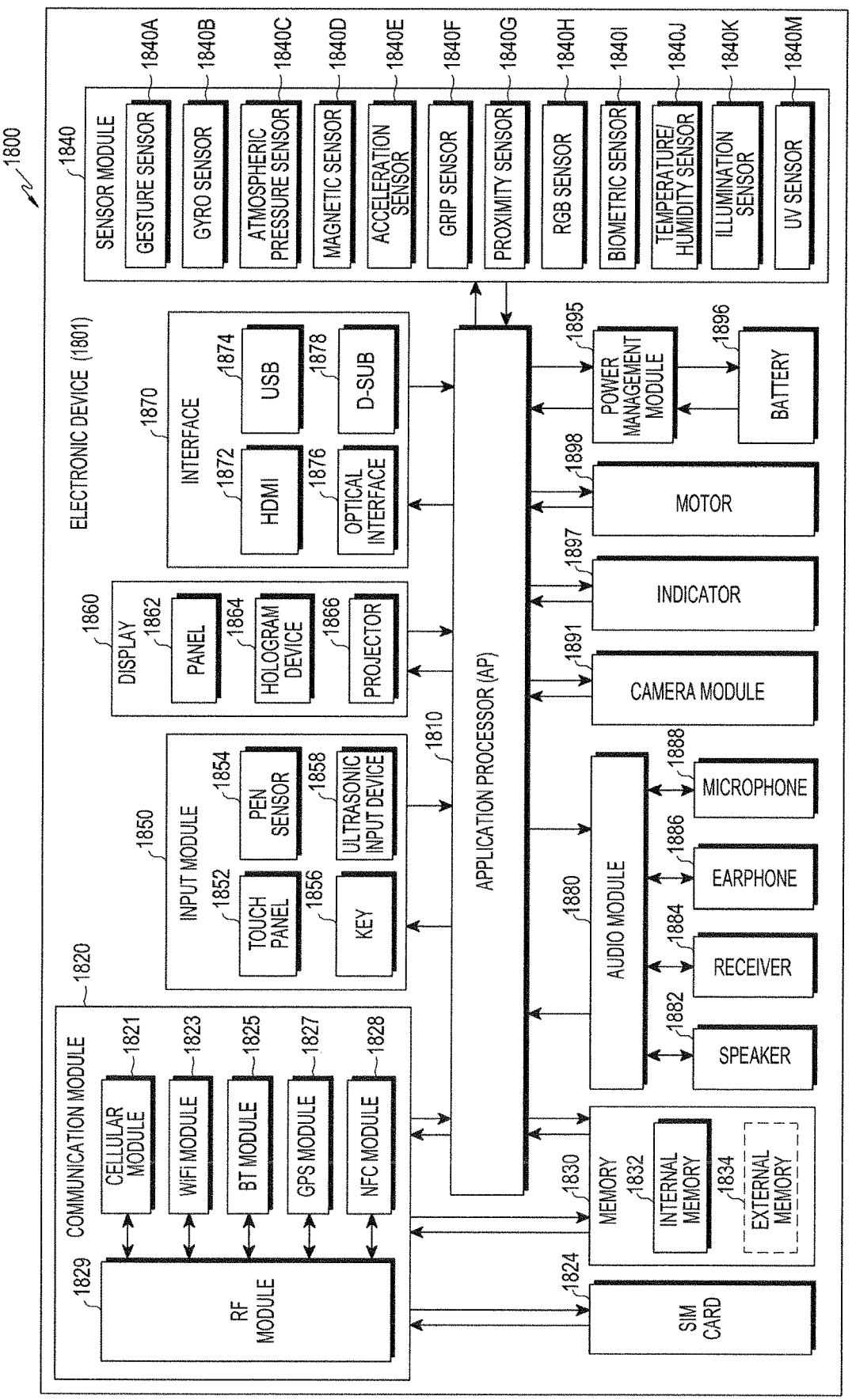
FIG. 18 is a block diagram illustrating an electronic device, according to an embodiment of the present invention.

FIG. 18 is a block diagram illustrating an electronic device, according to an embodiment of the present invention.

An electronic device 1800 may configure a part or the entirety of the electronic device 101 illustrated in FIG. 1. Referring to FIG. 18, the electronic device 1088 includes at least one application processor (AP) 1810, a communication module 1820, a subscriber identifier module (SIM) card 1824, a memory 1830, a sensor module 1840, an input module 1850, a display 1860, an interface 1870, an audio module 1880, a camera module 1891, a power management module 1895, a battery 1896, an indicator 1897, and a motor 1898.

The AP 1810 may control a plurality of hardware or software components connected to the AP 1810 by driving an operating system or an application program, process various types of data including multimedia data, and perform calculations. The AP 1810 may be implemented by, for example, a system on chip (SoC). According to an embodiment, the AP 1810 may further include a GPU.

The communication module 1820 (for example, the communication interface 160) may perform data transmission/reception in communication between the electronic device 1800 (for example, the electronic device 101) and other electronic devices (for example, the second external electronic device 104 or the server 106) connected over a network. According to an embodiment of the present invention, the communication unit 1820 includes a cellular module 1821, a WiFi module 1823, a BT module 1825, a GPS module 1827, a NFC module 1828, and a radio frequency (RF) module 1829.

The cellular module 1821 may provide a voice call, a video call, a text service, an Internet service, and the like, through a communication network (for example, LTE, LTE-A, CDMA, WCDMA, UMTS, WiBro, GSM, or the like). Also, the cellular module 1821 may identify and authenticate an electronic device in a communication network by using, for example, a subscriber identification module (for example, the SIM card 1824). According to an embodiment of the present invention, the cellular module 1821 may perform at least some of the functions which may be provided by the AP 1810. For example, the cellular module 1821 may perform at least a part of the multimedia control function.

According to an embodiment of the present invention, the cellular module 1821 may include a communication processor (CP). Also, the cellular module 1821 may be implemented by, for example, an SoC. Although the cellular module 1821 (for example, the communication processor), the memory 1830, and the power management module 1895 are illustrated as components separate from the AP 1810 in FIG. 18, the AP 1810 may be implemented to include at least some of the above described components (for example, the cellular module 1821), according to an embodiment of the present invention.

According to an embodiment of the present invention, the AP 1810 or the cellular module 1821 (for example, the communication processor) may load a command or data received from at least one of a non-volatile memory and other components connected thereto in a volatile memory, and process the loaded command or data. Further, the AP 1810 or the cellular module 1821 may store data received from or generated by at least one of the other components in a non-volatile memory.

Each of the Wi-Fi module 1823, the BT module 1825, the GPS module 1827, and the NFC module 1828 may include, for example, a processor for processing data transmitted/received through the corresponding module. Although the cellular module 1821, the Wi-Fi module 1823, the BT module 1825, the GPS module 1827, and the NFC module 1828 are illustrated as individual blocks in FIG. 18, at least some (for example, two or more) of the cellular module 1821, the Wi-Fi module 1823, the BT module 1825, the GPS module 1827, and the NFC module 1828 may be included within one integrated circuit (IC) or one IC package. For example, at least some of processors corresponding to the cellular module 1821, the WiFi module 1823, the BT module 1825, the GPS module 1827, and the NFC module 1828 (for example, a CP corresponding to the cellular module 1821 and a WiFi processor corresponding to the WiFi module 1823) may be implemented by one SoC.

The RF module 1829 may transmit/receive data, for example, an RF signal. Although not illustrated, the RF module 1829 may include, for example, a transceiver, a power amp module (PAM), a frequency filter, a low noise amplifier (LNA), or the like. Furthermore, the RF module 1829 may further include a component for transmitting/ receiving electronic waves over a free air space in wireless communication, for example, a conductor, a conducting wire, or the like. Although the cellular module 1821, the Wi-Fi module 1823, the BT module 1825, the GPS module 1827, and the NFC module 1828 are illustrated as sharing one RF module 1829 in FIG. 18, at least one of the cellular module 1821, the Wi-Fi module 1823, the BT module 1825, the GPS module 1827, and the NFC module 1828 may transmit/receive the RF signal through a separate RF module.

The SIM card 1824 may include a subscriber identification module, and may be insertable into a slot formed in a particular portion of the electronic device. The SIM card 1824 may include unique identification information (for example, an integrated circuit card identifier (ICCID)) or subscriber information (for example, an international mobile subscriber identity (IMSI)).

The memory 1830 (for example, the memory 130) includes at least one of an internal memory 1832 and an external memory 1834. The internal memory 1832 may include at least one of a volatile memory (for example, a dynamic RAM (DRAM), a static RAM (SRAM), a synchronous DRAM (SDRAM), and the like) and a non-volatile memory (for example, a one time programmable ROM (OTPROM), a programmable ROM (PROM), an erasable and programmable ROM (EPROM), an electrically erasable and programmable ROM (EEPROM), a mask ROM, a flash ROM, a NAND flash memory, a NOR flash memory, and the like).

According to an embodiment of the present invention, the internal memory 1832 may be a solid state drive (SSD). The external memory 1834 may further include a flash drive, for example, a compact flash (CF), a secure digital (SD), a Micro-SD, a Mini-SD, an extreme digital (xD), a memory stick, or the like. The external memory 1834 may be functionally connected to the electronic device 1800 through various interfaces. According to an embodiment of the present invention, the electronic device 1800 may further include a storage device (or storage medium), such as a hard drive.

The sensor module 1840 may measure a physical quantity or detect an operating state of the electronic device 1800, and convert the measured or detected information into an electrical signal. The sensor module 1840 includes, for example, at least one of a gesture sensor 1840A, a gyro sensor 1840B, an atmospheric pressure sensor 1840C, a magnetic sensor 1840D, an acceleration sensor 1840E, a grip sensor 1840F, a proximity sensor 1840G, a color sensor 1840H (for example, red, green, and blue (RGB) sensor), a biometric sensor 1840I, a temperature/humidity sensor 1840J, an illumination sensor 1840K, and an Ultra Violet (UV) sensor 1840M. Additionally or alternatively, the sensor unit 1840 may include, for example, an E-nose sensor, an electromyography (EMG) sensor, an electroencephalogram (EEG) sensor, an ECG sensor, an Infrared (IR) sensor, an iris sensor, a fingerprint sensor, and the like. The sensor unit 1840 may include at least one sensor that may sense or recognize the vital signal such as, a fingerprint, a foot fingerprint, an iris, a face, a heart rate, a brainwave, a joint, a pulse or the like. Further, the sensor module 1840 may include various sensors that may detect user's breathing as well as the plurality of aforementioned sensors. The sensor module 1840 may further include a control circuit for controlling one or more sensors included therein.

The input module 1850 includes at least one of a touch panel 1852, a (digital) pen sensor 1854, a key 1856, and an ultrasonic input device 1858. The touch panel 1852 may recognize a touch input in at least one type of, for example, a capacitive type, a resistive type, an infrared type, and an ultrasonic type. The touch panel 1852 may further include a control circuit. A capacitive touch panel may recognize a physical contact or proximity. The touch panel 1852 may further include a tactile layer. In this instance, the touch panel 1852 may provide a tactile reaction to a user.

The (digital) pen sensor 1854 may be implemented, for example, using a method identical or similar to receiving a user's touch input or using a separate recognition sheet. The key 1856 may include, for example, a physical button, an optical key or a keypad. The ultrasonic input device 1858 may detect an acoustic wave with a microphone (for example, a microphone 1888) of the electronic device 1800 through an input tool for generating an ultrasonic signal to identify data, and wireless recognition is possible therethrough. According to an embodiment, the electronic device 1800 may also receive a user input from an external device (for example, a computer or a server) connected thereto, using the communication unit 1820.

The display 1860 (for example, the display 150) includes at least one of a panel 1862, a hologram device 1864, and a projector 1866. The panel 1862 may be, for example, a liquid crystal display (LCD), an active matrix-organic light emitting diode (AM-OLED), or the like. The panel 1862 may be embodied to be, for example, flexible, transparent, or wearable. The panel 1862 may also be configured to be integrated with the touch panel 1852 as a single module. The hologram device 1864 may show a stereoscopic image in the air by using interference of light. The projector 1866 may project light onto a screen to display an image. For example, the screen may be located inside or outside the electronic device 1801. According to an embodiment of the present invention, the display 1860 may further include a control circuit for controlling the panel 1862, the hologram device 1864, or the projector 1866.

The interface 1870 includes, for example, at least one of an HDMI 1872, a USB 1874, an optical interface 1876, and a D-subminiature (D-sub) 1878. The interface 1870 may be included in, for example, the communication interface 160 illustrated in FIG. 1. Additionally or alternatively, the interface 290 may include, for example, a mobile high-definition link (MHL) interface, an SD card/multi-media Card (MMC) interface, or an infrared data association (IrDA) standard interface.

The audio module 1880 may bilaterally convert a sound and an electrical signal. At least some components of the audio module 1880 may be included in, for example, the input/output interface 140 of FIG. 1. The audio module 1880 may process sound information input or output through, for example, a speaker 1882, a receiver 1884, earphones 1886, the microphone 1888, or the like.

The camera module 1891 is a device capable of capturing a still image or a moving image and, according to an embodiment of the present invention, may include one or more image sensors (for example, a front sensor or a rear sensor), a lens, an image signal processor (ISP), or a flash (for example, an LED or xenon lamp).

The power management unit 1895 may manage power of the electronic device 1800. The power management unit 1895 may include, for example, a power management integrated circuit (PMIC), a charger IC, or a battery gauge.

The PMIC may be mounted to, for example, an integrated circuit or an SoC semiconductor. Charging methods may be classified into a wired charging method and a wireless charging method. The charger IC may charge a battery and prevent over voltage or over current from a charger. According to an embodiment of the present invention, the charger IC may include a charger IC for at least one of the wired charging method and the wireless charging method. Examples of the wireless charging may include magnetic resonance charging, magnetic induction charging, and electromagnetic charging, and an additional circuit such as a coil loop, a resonance circuit, and a rectifier may be added for the wireless charging.

The battery gauge may measure, for example, the residual quantity of the battery 1896, a charging voltage, current, or temperature. The battery 1896 may store or generate electricity, and may supply power to the electronic device 1800 using the stored or generated electricity. The battery 1896 may include, for example, a rechargeable battery or a solar battery.

The indicator 1897 may show particular statuses of the electronic device 1800 or a part (for example, the AP 1810) of the electronic device 1800, for example, a boot-up status, a message status, a charging status and the like. The motor 1898 may convert an electrical signal into mechanical vibration. The electronic device 1800 may include a processing device (for example, a GPU) for supporting mobile TV. The processing unit for supporting the mobile TV may process media data according to a standard of digital multimedia broadcasting (DMB), digital video broadcasting (DVB), media flow or the like.

Each of the components of the electronic device may be implemented by one or more components and the name of the corresponding component may vary depending on a type of the electronic device. The electronic device may be configured by including at least one of the above-described elements, and some of the elements may be omitted, or other elements may be added. Further, some of the elements of the electronic device may be combined to be one entity, which can perform the same functions as those of the elements before the combination.

Figure 19:
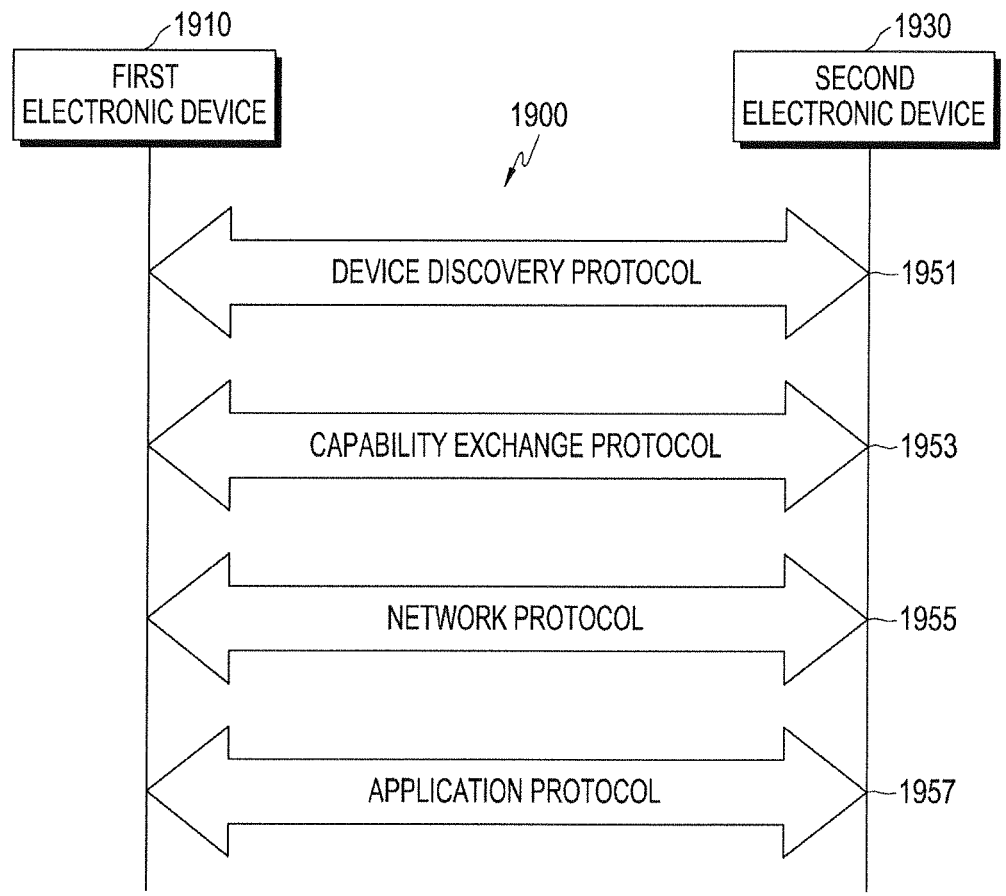
FIG. 19 is a diagram illustrating a communication protocol among a plurality of electronic devices, according to an embodiment of the present invention.

FIG. 19 is a diagram illustrating a communication protocol among a plurality of electronic devices, according to an embodiment of the present invention.

Referring to FIG. 19, a communication protocol 1900 includes a device discovery protocol 1951, a capability exchange protocol 1953, a network protocol 1955, and an application protocol 1957.

According to an embodiment of the present invention, the device discovery protocol 1951 may be a protocol that electronic devices (for example, a first electronic device 1910 or a second electronic device 1930) use to detect an external electronic device that is capable of communicating with the electronic devices or to connect to the detected external electronic device. For example, the first electronic device 1910 (for example, the electronic device 101) may sense the second electronic device 1930 (for example, the second external electronic device 104) through a communication method available in the first electronic device 1910 (for example, Wi-Fi, BT, USB, or the like), using the device discovery protocol 1951. For a communication connection with the second electronic device 1930, the first electronic device 1910 may acquire identification information of the second electronic device 1930 detected through the device discovery protocol 1951 and store the acquired identification information. The first electronic device 1910 may establish the communication connection with the second electronic device 1930, based on, for example, at least the identification information.

According to an embodiment of the present invention, the device discovery protocol 1951 may be a protocol for a mutual authentication among a plurality of electronic devices. For example, the first electronic device 1910 may execute authentication between the first electronic device 1910 and the second electronic device 1930, based on communication information (for example, a media access control (MAC) address, a universally unique identifier (UUID), a subsystem identification (SSID), and an IP address) for a connection with at least one second electronic device 1930.

According to an embodiment of the present invention, the capability exchange protocol 1953 is a protocol for exchanging information associated with a function of a service that may be supported by at least one of the first electronic device 1910 and the second electronic device 1930. For example, the first electronic device 1910 and the second electronic device 1930 may exchange information associated with a function of a service that each electronic device currently provides, through the capability exchange protocol 1953. The information that may be exchanged may include identification information indicating a predetermined service from among a plurality of services that may be provided in the first electronic device 1910 and the second electronic device 1930. For example, the first electronic device 1910 may receive, from the second electronic device 1930, identification information of a predetermined service provided by the second electronic device 1930, through the capability exchange protocol 1953. In this instance, the first electronic device 1910 may determine whether the first electronic device 1910 supports the predetermined service based on the received identification information.

According to an embodiment of the present invention, the network protocol 1955 may be a protocol to control data flow, for example, which is transmitted or received between electronic devices connected for communication (for example, the first electronic device 1910 and the second electronic device 1930), to provide services by working together. For example, at least one of the first electronic device 1910 and the second electronic device 1930 may execute error control, data quality control, or the like, using the network protocol 1955. Additionally or alternatively, the network protocol 1955 may determine a transport format of data transmitted/received between the first electronic device 1910 and the second electronic device 1930. Also, at least one of the first electronic device 1910 and the second electronic device 1930 may manage at least a session (connect the session or terminate the session) for exchanging data between them using the network protocol 1955.

According to an embodiment of the present invention, the application protocol 1957 may be a protocol for providing a process or information for exchanging data related to a service provided to an external electronic device. For example, the first electronic device 1910 (for example, the electronic device 101) may provide a service to the second electronic device 1930 (for example, the electronic device 104 or the server 106) through the application protocol 1957.

According to an embodiment of the present invention, the communication protocol 1900 may include a standard communication protocol, a communication protocol designated by an individual or organization (for example, a communication protocol self-designated by a communication device manufacturing company, a network supplying company, or the like) or a combination thereof.

The term "module", as used herein, may refer to, for example, a unit including one or more combinations of hardware, software, and firmware. The term "module" may be interchangeable with terms, such as unit, logic, logical block, component, or circuit. A module may be a minimum unit of an integrated component element or a part thereof. A module may be a minimum unit for performing one or more functions or a part thereof. A module may be mechanically or electronically implemented. For example, a module, according to an embodiment the present invention, may include at least one of an application specific integrated circuit (ASIC) chip, a field-programmable gate array (FPGA), and a programmable-logic device for performing operations.

According to an embodiment of the present invention, at least some of the devices (for example, modules or functions thereof) or the method (for example, operations) may be implemented by a command stored in a computer-readable storage medium in a programming module form. When the instruction is performed by at least one processor (for example, the processor 120), the at least one processor may perform a function corresponding to the instruction. The computer-readable storage medium may be, for example, the memory 18. At least some of the programming modules may be implemented (for example, executed) by, for example, the processor 120. At least some of the programming modules may include, for example, a module, a program, a routine, a set of instructions or a process for performing one or more functions.

The computer-readable recording medium may include magnetic media such as a hard disk, a floppy disk, and a magnetic tape, optical media such as a compact disc-ROM (CD-ROM) and a DVD, magneto-optical media such as a floptical disk, and hardware devices specially configured to store and perform a program instruction (for example, programming module), such as a ROM, a RAM, a flash memory, and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

The programming module, according to embodiments of the present invention, may include one or more of the aforementioned components or may further include other additional components, or some of the aforementioned components may be omitted. Operations executed by a module, a programming module, or other component elements, according to embodiments of the present invention, may be executed sequentially, in parallel, repeatedly, or in a heuristic manner. Further, some operations may be executed according to another order or may be omitted, or other operations may be added. According to an embodiment of the present invention, a storage medium having commands stored therein is provided. The commands are configured to allow one or more processors to perform one or more operations when executed. The operations may include a first command set for detecting a motion of an electronic device, a second command set for measuring a vital signal at least one time when the detected motion is smaller than or equal to a threshold, a third set for analyzing a parameter of the measured vital signal, and a fourth command set for converting the analyzed parameter into vital information.

While the invention has been shown and described with reference to certain embodiments thereof, it will be understood by those skilled in the art that various changes in form and detail may be made therein without departing from the spirit and scope of the invention as defined by the appended claims.

What is claimed is:

1. A method of measuring a biometric signal by an electronic device, the method comprising:
   executing an application related to biometric information of a user wearing the electronic device;
   displaying, on a display of the electronic device, an object having an animation effect for inhalation and exhalation while the application is executed, the animation effect including the object being expanded to guide the inhalation of the user and the object being contracted to guide exhalation of the user;
   obtaining, by a sensor unit of the electronic device, at least one biometric signal related to a heart rate of the user while the object having the animation effect is displayed; and
   displaying, on the display of the electronic device, the biometric information corresponding to the obtained at least one biometric signal,
   wherein the method further comprises:
      detecting a motion of the electronic device having a strength that is greater than or equal to a threshold strength;
      based on the motion of the electronic device ceasing before exceeding a predetermined time, continuing to display the object and obtain the at least one biometric signal; and
      based on the motion of the electronic device lasting longer than or equal to the predetermined time:
         terminating the obtaining of the at least one biometric signal; and
         terminating the displaying of the object, wherein the biometric information is not displayed.

2. The method of claim 1, wherein displaying the object further comprises:
   displaying, on the display of the electronic device, a text that guides the inhalation and the exhalation with the object.

3. The method of claim 1, wherein the animation effect guides a depth of each inhalation and each exhalation of the user.

4. The method of claim 1, further comprising:
   initiating a breathing guide on the electronic device,
   wherein the breathing guide is initiated in response to a determination that biometric information previously measured by the electronic device is higher than comparable biometric information for users in a same age range.

5. The method of claim 1, wherein displaying the biometric information comprises displaying, by the display of the electronic device, the biometric information corresponding to the at least one biometric signal in real time.

6. The method of claim 1, wherein displaying the biometric information comprises displaying the biometric information in a graphical form over time.

7. The method of claim 1, wherein obtaining at least one biometric signal comprises:
   obtaining the at least one biometric signal for the user for a preset time,
   wherein the preset time is adjustable.

8. An electronic device for measuring a biometric signal, the electronic device comprising:
   a display;
   a sensor unit configured to obtain at least one biometric signal; and
   at least one processor configured to:
      execute an application related to biometric information of a user wearing the electronic device;
      display, on the display, an object having an animation effect for inhalation and exhalation while the application is executed, the animation effect including the object being expanded to guide the inhalation of the user and the object being contracted to guide the exhalation of the user;

obtain, via the sensor unit, at least one biometric signal related to a heart rate of the user while the object having the animation effect is displayed; and display, on the display, biometric information corresponding to the obtained at least one biometric signal, wherein the at least one processor is further configured to:

detect a motion of the electronic device having a strength that is greater than or equal to a threshold strength;

based on the motion of the electronic device ceasing before exceeding a predetermined time, continue to display the object and obtain the at least one biometric signal; and based on the motion of the electronic device lasting longer than or equal to the predetermined time:

terminate the obtaining of the at least one biometric signal; and terminate the displaying of the object, wherein the biometric information is not displayed.

9. The electronic device of claim 8, wherein the at least one processor is further configured to:

display, on the display, a text that guides the inhalation and exhalation with the object.

10. The electronic device of claim 8, wherein the animation effect guides a depth of each inhalation and each exhalation of the user.

11. The electronic device of claim 8, wherein the at least one processor is further configured to:

initiate a breathing guide on the electronic device, wherein the breathing guide is initiated in response to a determination that biometric information previously measured by the electronic device is higher than comparable biometric information for users in a same age range.

12. The electronic device of claim 11, wherein the previously measured biometric information comprises at least a heart rate of the user.

13. The electronic device of claim 11, wherein the at least one processor is further configured to:

detect breathing of the user by the electronic device or receiving information on detected breathing;

compare the detected breathing with a breathing quantity proposed by the breathing guide; and display, on the display of the electronic device, a result of the comparison in real time.

14. The electronic device of claim 8, wherein, to display the biometric information, the at least one processor is further configured to transmit the biometric information to another electronic device.

15. The electronic device of claim 8, wherein, to display the biometric information, the at least one processor is further configured to display, by the display of the electronic device, the biometric information corresponding to the at least one biometric signal in real time.

16. The electronic device of claim 8, wherein, to display the biometric information, the at least one processor is further configured to display the biometric information in a graphical form over time.

17. The electronic device of claim 8, wherein the at least one processor is further configured to:

obtain, via the sensor unit, the at least one biometric signal for the user for a preset time, wherein the preset time is adjustable.

18. A non-transitory computer readable medium with computer executable instructions stored thereon executed by at least one processor to perform the method of measuring a biometric signal by an electronic device, the method comprising:

executing an application related to biometric information of a user wearing the electronic device;

displaying, on a display of the electronic device, an object having an animation effect for inhalation and exhalation while the application is executed, the animation effect including the object being expanded to guide the inhalation of the user and the object being contracted to guide the exhalation of the user;

obtaining, by a sensor unit of the electronic device, at least one biometric signal related to a heart rate of the user while the object having the animation effect is displayed; and displaying, on the display, biometric information corresponding to the obtained at least one biometric signal, wherein the method further comprises:

detecting a motion of the electronic device having a strength that is greater than or equal to a threshold strength;

based on the motion of the electronic device ceasing before exceeding a predetermined time, continuing to display the object and obtain the at least one biometric signal; and based on the motion of the electronic device lasting longer than or equal to the predetermined time:

terminating the obtaining of the at least one biometric signal; and terminating the displaying of the object, wherein the biometric information is not displayed.

* * * * *